(12) United States Patent
Radne et al.

(10) Patent No.: US 11,141,323 B2
(45) Date of Patent: *Oct. 12, 2021

(54) DISPOSABLE HYGIENE ARTICLE WITH IMPROVED FIT

(71) Applicant: Essity Hygiene and Health Aktiebolag, Gothenburg (SE)

(72) Inventors: Viktoria Radne, Gothenburg (SE); Josefin Sohl, Gothenburg (SE); Anna Bagger-Sjöbäck, Gothenburg (SE); Sofia Ekstedt, Gothenburg (SE)

(73) Assignee: Essity Hygiene and Health Aktiebolag, Gothenburg (SE)

( * ) Notice: Subject to any disclaimer, the term of this patent is extended or adjusted under 35 U.S.C. 154(b) by 0 days.

This patent is subject to a terminal disclaimer.

(21) Appl. No.: 16/618,969

(22) PCT Filed: Jun. 9, 2017

(86) PCT No.: PCT/SE2017/050612
§ 371 (c)(1),
(2) Date: Dec. 3, 2019

(87) PCT Pub. No.: WO2018/226133
PCT Pub. Date: Dec. 13, 2018

(65) Prior Publication Data
US 2020/0163809 A1 May 28, 2020

(51) Int. Cl.
*A61F 13/47* (2006.01)
*A61F 13/15* (2006.01)
(Continued)

(52) U.S. Cl.
CPC .... *A61F 13/4704* (2013.01); *A61F 13/15577* (2013.01); *A61F 13/475* (2013.01); *A61F 13/532* (2013.01); *A61F 2013/8402* (2013.01)

(58) Field of Classification Search
CPC .............. A61F 13/533; A61F 13/4704; A61F 2013/5108
See application file for complete search history.

(56) References Cited

U.S. PATENT DOCUMENTS

| 4,501,586 A * | 2/1985 | Holtman ............... A61F 13/535 604/380 |
| 4,765,780 A | 8/1988 | Angstadt |

(Continued)

FOREIGN PATENT DOCUMENTS

| CN | 1496720 A | 5/2004 |
| CN | 1809326 A | 7/2006 |

(Continued)

OTHER PUBLICATIONS

China National Intellectual Property Administration, Notification of the First Office Action, Application No. 201780091783.0, dated May 8, 2020 (25 pages).

(Continued)

*Primary Examiner* — Catharine L Anderson
*Assistant Examiner* — Arjuna P Chatrathi
(74) *Attorney, Agent, or Firm* — Wood Herron & Evans LLP

(57) ABSTRACT

A disposable hygiene article having an absorbent core with a first region which has its narrowest width (M) in the transverse direction (x) in a front portion or at a location of a transition between the front portion and a crotch portion of the article. The absorbent core comprises a high-density first region and a low density second region. The absorbent core in the crotch region has first and second rear compression lines. The compression lines mutually diverge in a direction towards the core front edge. Each line has a diverging angle ($\alpha_2$; $\alpha_3$) of from 15-60° with respect to a centre line (A). The (Continued)

second region has an average density which is at least 20% lower than the average density of the first region.

32 Claims, 8 Drawing Sheets

(51) Int. Cl.
*A61F 13/475* (2006.01)
*A61F 13/532* (2006.01)
*A61F 13/84* (2006.01)

(56) References Cited

U.S. PATENT DOCUMENTS

| | | | | |
|---|---|---|---|---|
| 5,149,334 | A | * | 9/1992 | Lahrman ............... A61F 13/535 604/367 |
| 5,300,054 | A | * | 4/1994 | Feist ................ A61F 13/15203 604/358 |
| 5,312,386 | A | * | 5/1994 | Correa ................ A61F 13/4752 604/379 |
| 5,387,208 | A | * | 2/1995 | Ashton ................ A61F 13/531 604/358 |
| 5,591,149 | A | * | 1/1997 | Cree ................ A61F 13/47218 604/368 |
| 6,486,379 | B1 | * | 11/2002 | Chen .................. A61F 13/4704 604/378 |
| 6,660,902 | B2 | | 12/2003 | Widlund et al. |
| 6,986,761 | B1 | * | 1/2006 | Hines ................ A61F 13/4704 604/385.01 |
| 2003/0130643 | A1 | * | 7/2003 | Drevik ............. A61F 13/47272 604/385.31 |
| 2005/0004547 | A1 | | 1/2005 | Lavash |
| 2005/0182374 | A1 | | 8/2005 | Zander et al. |
| 2009/0292268 | A1 | * | 11/2009 | Bagger-Sjoback ........................ A61F 13/47218 604/385.01 |
| 2011/0319851 | A1 | * | 12/2011 | Kudo ................ A61F 13/4756 604/380 |

FOREIGN PATENT DOCUMENTS

| | | |
|---|---|---|
| CN | 101484117 A | 7/2009 |
| CN | 105828761 A | 8/2016 |
| DE | 4004729 A1 | 8/1990 |
| EP | 1035818 A1 | 9/2000 |
| EP | 1253231 A2 | 10/2002 |
| EP | 1493413 A2 | 1/2005 |
| EP | 2092918 A1 | 8/2009 |
| EP | 2103291 B1 | 2/2013 |
| EP | 1402863 B2 | 7/2013 |
| EP | 2934408 A1 | 10/2015 |
| JP | H11113955 A | 4/1999 |
| JP | 2006239162 A | 9/2006 |
| JP | 2011125537 A | 6/2011 |
| JP | 2014195529 A | 10/2014 |
| JP | 2015104645 A | 6/2015 |
| JP | 2015112268 A | 6/2015 |
| JP | 2016049197 A | 4/2016 |
| JP | 2018051110 A | 4/2018 |
| SE | 9401542 L | 11/1995 |
| WO | 9507674 A2 | 3/1995 |
| WO | 9515139 A1 | 6/1995 |
| WO | 2005079722 A1 | 9/2005 |
| WO | 2007008125 A1 | 1/2007 |
| WO | 2008004961 A1 | 1/2008 |
| WO | 2008078805 A1 | 7/2008 |
| WO | 2012057332 A1 | 5/2012 |
| WO | 2012133331 A1 | 10/2012 |
| WO | 2014155757 A1 | 10/2014 |
| WO | 2016031418 A1 | 3/2016 |
| WO | 2017217356 A1 | 12/2017 |
| WO | 2018226131 A1 | 12/2018 |
| WO | 2018226133 A1 | 12/2018 |

OTHER PUBLICATIONS

National Intellectual Property Administration (CNIPA) of The People's Republic of China, Notification of The First Office Action, Application No. 201780091799.1, dated Apr. 7, 2020 (15 pages).
International Preliminary Report on Patentability for International Application No. PCT/SE2017/050610, dated May 22, 2019, 15 pages.
International Preliminary Report on Patentability for International Application No. PCT/SE2017/050611, dated May 17, 2019, 6 pages.
International Preliminary Report on Patentability for International Application No. PCT/SE2017/050612, dated May 17, 2019, 6 pages.
International Search Report and Written Opinion for International Application International Preliminary Report on Patentability for International Application No. PCT/SE2017/050610, dated Feb. 13, 2018, 14 pages.
International Search Report and Written Opinion for International Application International Preliminary Report on Patentability for International Application No. PCT/SE2017/050611, dated Feb. 13, 2018, 12 pages.
International Search Report and Written Opinion for International Application International Preliminary Report on Patentability for International Application No. PCT/SE2017/050612, dated Feb. 13, 2018, 13 pages.
Patent-OCH Registreringsverket, International Search Report and Written Opinion of the International Searching Authority, International Application No. PCT/SE2018/051252, dated Aug. 28, 2019, 13 pages.
Patent-OCH Registreringsverket, International Search Report and Written Opinion of the International Searching Authority, International Application No. PCT/SE2018/051254, dated Aug. 28, 2019, 13 pages.
Patent-OCH Registreringsverket, International Search Report and Written Opinion of the International Searching Authority, International Application No. PCT/SE2018/051255, dated Aug. 28, 2019, 13 pages.
National Intellectual Property Administration (CNIPA) of the People's Republic of China, Notification of the First Office Action, Application No. 201780091784.5, dated Mar. 8, 2021 (26 pages).

* cited by examiner

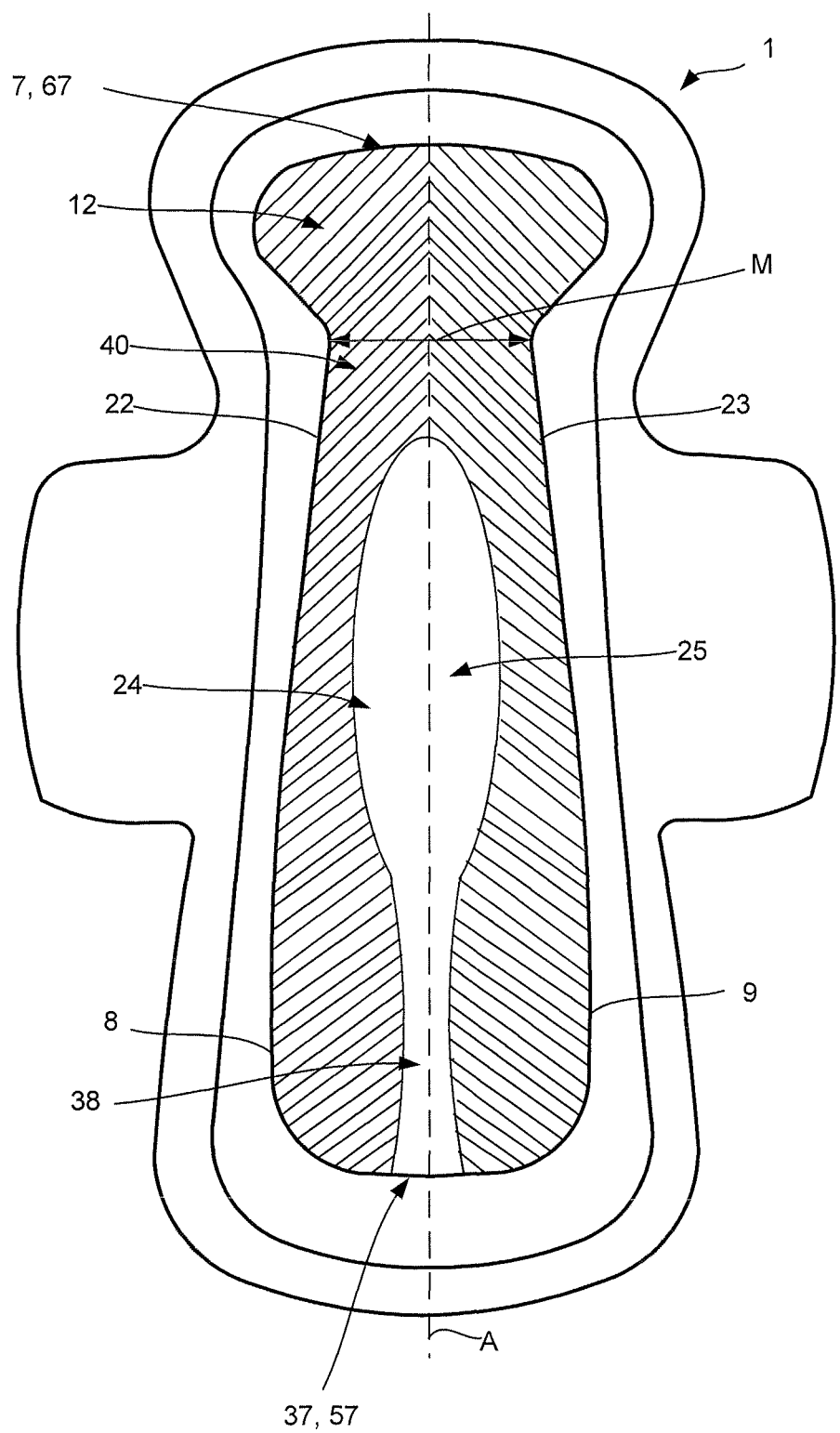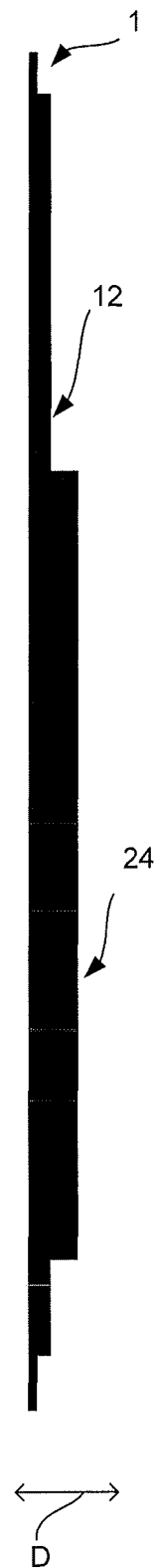
Fig. 6
Fig. 7

DISPOSABLE HYGIENE ARTICLE WITH IMPROVED FIT

CROSS REFERENCE TO RELATED APPLICATIONS

This is a U.S. National Phase application of PCT/SE2017/050612, filed Jun. 9, 2017, the disclosure of which is incorporated herein by reference in its entirety for all purposes.

TECHNICAL FIELD

The present invention relates to disposable hygiene articles, such as sanitary towels, panty liners, incontinence pads or diapers which are designed so that they adopt a particular form when in use to provide improved fit and security against leakage. The present invention also relates to a method for the manufacture of the disposable hygiene article.

BACKGROUND

Disposable hygiene articles need to have good absorptive properties, comfort and need to provide a sense of leakage security and good fit for a user. Various designs and methods have been employed in hygiene articles so that they could follow the contours of the user's body well and do not move out of place during use. For example in the applicant's own previous application WO 2008/004961 A1 an absorbent article with improved fit has been shown. The absorbent article comprises an absorbent core comprising a first region with two legs extending in the longitudinal direction of the article over at least parts of the crotch portion towards separate leg endings in the rear portion. The legs are arranged symmetrically about a longitudinal centre line and a distance between facing sides of the respective legs in the transverse direction varies in the longitudinal direction. A maximum distance is in the crotch portion, located at a position in the longitudinal direction corresponding to a position of a crotch point. The facing sides of the respective legs converge backwards in the longitudinal direction such that the distance is reduced from said maximum distance to a minimum distance in the rear portion. The absorbent core further comprises a second region surrounding said first region and extending between said first region and a circumferential edge of the article. The average density of the absorbent core in the second region is lower than the average density in the first region. By the design promoted leakage security with good fit and correct, secure placement of the article are obtained. However, despite the efforts to improve the fit of the article, there is still a need to further improve the fit of the article and how the article conforms to the body of the user. Furthermore, there is a need for a simple manufacture method of such products in the existing equipment.

SUMMARY

It has been found that despite prior art solutions for disposable hygiene articles there is still a need to improve fit of the article and especially how the article conforms to the body of the user. There is a need to better control how the article bends and conforms to the body especially in respect to the rear portion and crotch portion comprising a centre region of the article. It is important that good and close fit to the body is obtained in the front, crotch and rear portion of the article. Also, it is of importance that the existing equipment can be used for the manufacture of the articles with minimal amount of modifications.

The objective of the present disclosure is thus to provide a disposable hygiene article with improved fit of the article and improved way the article conforms to the body of the user. It is an objective to provide an article which conforms to the body in an improved manner in the rear portion of the article. It also an object to provide good fit in the front and crotch portion of the article.

Also, it is an objective of the present invention to provide a disposable and absorbent hygiene article with improved comfort, while the absorbency of the article is satisfactory. The disposable hygiene article may be a sanitary towel, a panty liner, an incontinence pad or a diaper.

Furthermore, it is an objective of the present disclosure to provide disposable hygiene article which can be easily manufactured in the existing equipment with minimal amount of modifications.

The objectives above are achieved by the present disposable hygiene article as defined in the appended claims.

Thus, the present invention relates to a disposable hygiene article, such as a sanitary towel, a panty liner, an incontinence pad or a diaper, said article has a transverse direction, a longitudinal direction and a longitudinal centre line dividing the article into two mutually symmetrical and mirror-imaged portions. Said article has a front portion, a crotch portion and a rear portion. Said article comprises a liquid-permeable topsheet, a liquid-impermeable backsheet, an absorbent core arranged between the topsheet and backsheet and optionally a liquid acquisition sheet arranged between the topsheet and the core. An outer contour of the absorbent core is defined by mirror-imaged first and second core edge lines, and the core is delimited by a core front edge in the front portion and a core rear edge in the rear portion. Said absorbent core comprises a first region extending in the longitudinal direction of the article from a first region front edge in the front portion over the crotch portion to the rear portion. The outer contour of the first region is defined by mirror-imaged first and second first region edge lines. The first region comprises a head part and two leg portions extending symmetrically about the centre line and in a longitudinal direction of the article, starting and diverging from a common leg portion start point in the crotch portion and extending over a portion of the crotch portion towards separate leg portion endings in the rear portion. A distance between facing sides of the respective leg portions in the transverse direction varies in the longitudinal direction, whereby a maximum distance between the facing sides of the respective leg portions in the transverse direction is in the crotch portion, located at a position in the longitudinal direction corresponding to a position of a crotch point. Said facing sides of the respective leg portions converge backwards in the longitudinal direction such that said distance is reduced from said maximum distance to a minimum distance. Said absorbent core further comprises a second region at least partially surrounded by said first region and extending between said leg portions in the transverse direction and in the length direction from the leg portion start point in the crotch portion to an end point in the rear portion. The first region has its narrowest width in the transverse direction in the front portion or at the location of a transition between the front portion and the crotch portion. Further, the absorbent core in the crotch portion comprises a first rear compression line and a second rear compression line, wherein the lines mutually diverge in a direction towards the core front edge. Each of the lines has a diverging angle of from 15-60° in respect of the extension of the centre line. The lines have an extension up to the respective first and second first region edge lines and/or the respective first and second core edge lines. Further, the second region has an average density which is at least 20%, preferably at least 30% and most preferably at least 50% lower than the average density of the first region. By having a higher density and thus stiffness in the first region while the rear compression lines promote transverse and diagonal bending of the rear part of the article towards the body of the user during use, the fit of the product is improved in the crotch and rear portion of the article. Also, the article will be kept in its position during use in an improved manner.

The front and rear compression lines are straight lines or essentially straight lines produced by means of a groove or line compression tool having a shape of a straight line. However, in the product due to the nature of compressible materials used in absorbent articles minor variations may be possible.

The first and second rear compression lines can be distanced from each other in the transverse direction and are thus free from a common rear tip. In this way, for example a rear section of the article can be left intact.

According to another variant, the first and second rear compression lines may form a V-shape comprising a common rear tip in which the lines, i.e. the first and second rear compression lines, meet. The rear tip suitably has an imaginary contact point with an imaginary rear division line dividing the article into the crotch portion and the rear portion. In this way, the product will bend more effectively at an area outside a centre region of the second region.

The absorbent core may in the crotch portion further comprise at least one compression line forming an essentially upside down turned V comprising a first leg and a second leg and a common front tip. The front tip is suitably located on the centre line and has an imaginary contact point with an imaginary front division line dividing the article into the front portion and the crotch portion. The first and second legs suitably diverge towards the core rear edge at a mutual angle of from 30-120°, and the legs extend up to the respective first and second first region edge lines or core edge lines. By having a higher density and thus stiffness in the first region while the front compression lines promote transverse and diagonal bending of the front part of the article towards the body of the user during use, the fit of the product is improved further in the crotch portion and also in the front portion of the article. Also, the article will be kept in its position during use in an improved manner.

The front tip can be distanced from the crotch point by 40-80 mm. Therefore, it can be assured that the wetting area is not bent during the use, whereby the absorption properties are not negatively affected.

The compression lines can be obtained by means of groove or line compressing the core and optionally the acquisition sheet and/or the topsheet with high pressure compression from the topsheet or the backsheet side of the article. In this way all the layers are embossed to further promote the bending characteristic of the article during use. Alternatively, the backsheet is not compressed.

The second region may comprise a centre region extending symmetrically about the centre line and having a longer extension in the longitudinal direction than in the transverse direction, and a longitudinally and symmetrically about the centre line extending rear section in contact with the centre region. The centre region and the rear section are limited by the facing sides of the respective leg portions. Thus, the centre region can provide at least a portion of a wetting area of the article.

The centre region may comprise a weakening compression line extending along the centre line between a start point and a centre region end point. In this way, bending of the centre region longitudinally towards the genitals of the user during use can be further promoted.

A maximum width of the centre region can be 10-50 mm and a length is from 50-110 mm. In this way, liquid absorption properties in a wetting area of the article can be improved. The minimum width of a rear section, which is limited by the facing sides of the respective leg portions, can be from 5-30 mm and a length can be from 30-110 mm. In this way, the fit of the rear section to the body of the user can be improved.

The centre region may extend in a thickness direction of the article such that it protrudes outwards from a plane of the first region. In this way a raised portion is provided, which may in an easy way be in contact with genitals of the user during use.

The first region can have an average density of an absorbent material from 150-220 $kg/m^3$, preferably from 160-210 $kg/m^3$. The second region can have an average density of an absorbent material from 70-150 $kg/m^3$, preferably from 80-130 $kg/m^3$. How the density is measured is described later in the detailed description, which is herein referred to. How the density is measured is described later in the detailed description, which is herein referred to. The lower density region provides for quick inlet of liquid into the core while the higher density provides for better liquid distribution and also enables taking up of liquid in a repeated manner. Thus the whole capacity of the core can be better utilized. The low density areas also make it possible to omit the acquisition layer from the article.

The first region is suitably compressed more than the second region, and the first region is stiffer than the second region. Thus, the first region obtains a higher average density of an absorbent material in at least a portion of the first region than in the second region. In this way the bending properties of the article can be controlled in a pre-determined way.

The higher average density of the absorbent material can be obtained by means of compression and/or providing an embossing pattern to the first region which covers at least portion of the first region, and wherein the second region is free of the embossing pattern. In this way the article can be easily manufactured, while the stiffness properties can be controlled in a desirable way.

The embossing pattern may comprise individual dots placed in a predetermined pattern. In this way also aesthetically pleasant product can be provided.

The disposable hygiene article may further comprise a liquid acquisition sheet located between the topsheet and the core. In this way liquid distribution characteristics can be improved. The liquid acquisition sheet may be composed of airlaid nonwoven having a grammage of from 50-100 gsm (grams per square meter). Alternatively, the liquid acquisition sheet may be composed of spunlace nonwoven having a grammage of from 30-90 gsm. Further, the liquid acquisition sheet may be composed of high loft fibrous material having a grammage of from 30-90 gsm. Different materials provide different properties, e.g. by using airlaid or spunlace a thin product can be provided, while with high loft a more bulky product can be provided.

The liquid acquisition sheet may have a larger extension than the core in both the transverse and longitudinal extension of the core and is located in contact with the core. In this way an article with high comfort can be provided. Also, the visual appearance of the article may be improved, since the liquid acquisition sheet covers and in this way hides potentially uneven edges of the core.

According to a variant, the liquid acquisition sheet may be composed of high loft fibrous material. The first region of the core can be embossed while edge regions of the liquid acquisition sheet can be free of an embossing pattern and/or compression. In this way, an article with soft sides can be provided.

The narrowest width of the first region of the core in said front portion is suitably from 15 to 45 mm in the transverse direction. In this way the article can be anchored between muscle tendons of the user that form part of the muscle group which originates on the inside of the pelvic diaphragm and has its attachment along the thigh. The anchoring can thus occur in an optimal way.

The second region may cover from 10-50% of a total area of the core. In this way, a soft area can be provided while the bending of the article can be controlled.

The location of the smallest width of the core can be distanced from the front tip in a longitudinal direction by 0-10 mm. In this way, improved bending properties for the front portion can be provided. The front tip can be distanced from the crotch point by 40-80 mm. Therefore, it can be assured that the wetting area is not bent during the use, whereby the absorption properties are not negatively affected.

The present invention further relates to a method for the manufacture of the disposable article described above, the method comprising the steps of:
  feeding a liquid-permeable topsheet material layer, a liquid-impermeable backsheet material layer and an absorbent material layer arranged to be positioned in between the topsheet material layer and the backsheet material layer, and optionally and an acquisition material layer arranged to be positioned between the topsheet material layer and the absorbent material layer;
  forming the first region and second region of the core by compressing the first region more than the second region and/or by embossing an embossing pattern to areas providing the first region in the core from the side of the topsheet layer, and a further step of providing a first rear compression line and a second rear compression line, wherein the lines mutually diverge in a direction towards the core front edge, and each of the lines has an diverging angle of from 15-60° in respect of the extension of the centre line, wherein the lines have an extension up to the respective first and second first region edge lines and/or the respective first and second core edge lines and optionally a further front compression line, by means of high pressure compression from the topsheet or the backsheet side of the core;
  optionally providing a weakening compression line extending along the centre line between a start point $a_0$ and a centre region end point $a_e$.

In the method the first region can be formed prior to marriage of the backsheet to the absorbent core, topsheet and optionally liquid acquisition sheet of the article.

Further objectives, features and advantages of the present disposable hygiene article and the method for the manufacture of the article are described in the detailed description below with reference to the appended drawings.

BRIEF DESCRIPTION OF THE DRAWINGS

FIG. 6 schematically shows the first region and second region in disposable hygiene article according to the present disclosure;

FIG. 7 shows a side view of the disposable hygiene article of FIG. 6;

DETAILED DESCRIPTION OF PARTICULAR EMBODIMENTS

Figure 1:
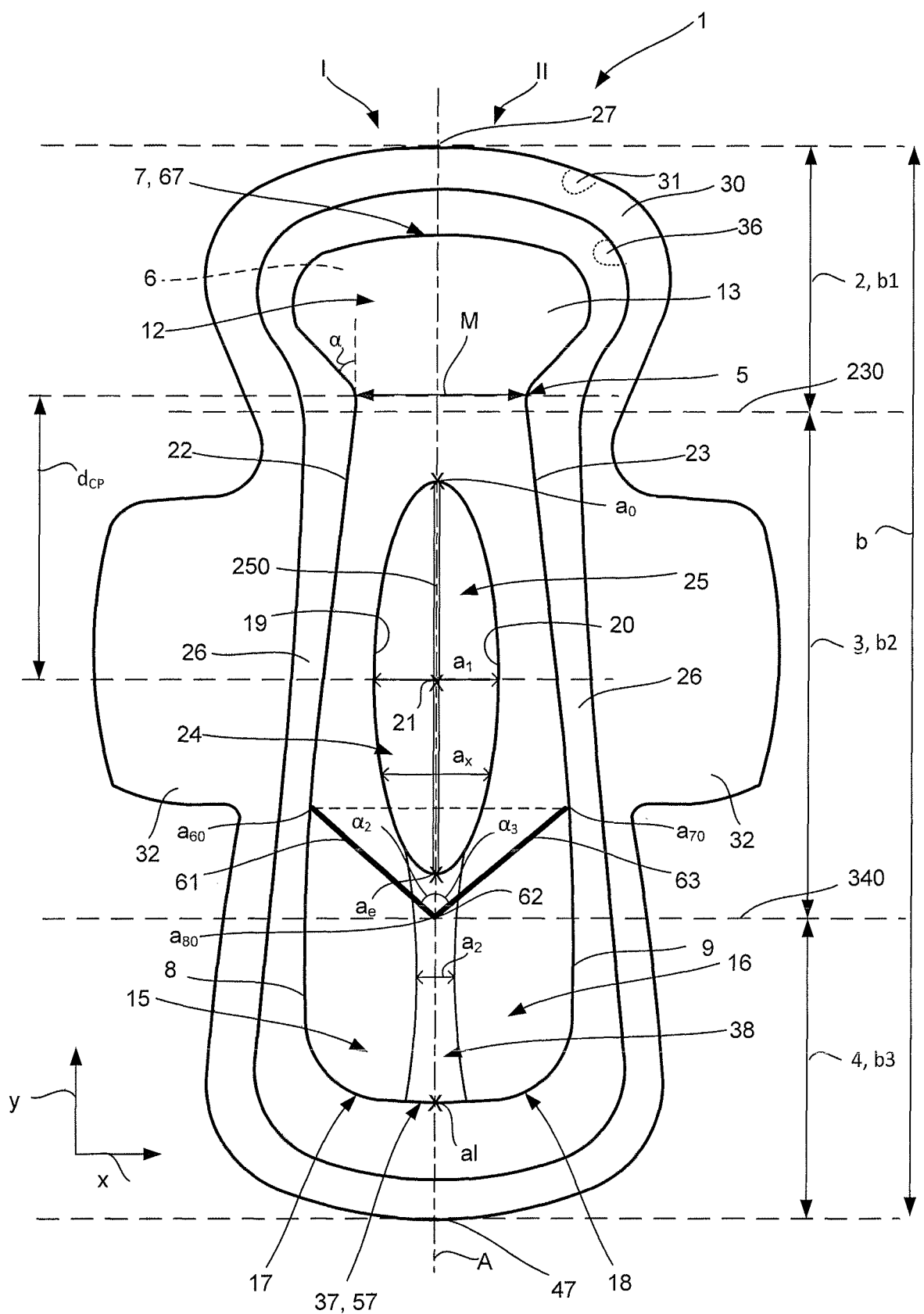
FIG. 1 shows schematically a plan view of an example disposable hygiene article according to the present disclosure.

The present disposable hygiene article is an absorbent article aimed for personal hygiene and may be for example a sanitary towel, a panty liner, an incontinence pad or a diaper. Such articles are commonly used for acquisition and storage of bodily exudates such as urine, faeces or menstrual fluid. The absorbent article is disposable, which means that it is intended to be used only once and disposed thereafter, rather than being cleaned and re-used. The absorbent article may suitably be a sanitary towel, and the design of the article is particularly suitable for sanitary towels.

Each of FIGS. 1 to 6 and 8 shows a plan view of an embodiment, which is a sanitary towel, of the disposable hygiene article 1 according to the present disclosure. All embodiments of the present disposable hygiene article 1 have a transverse direction x, a longitudinal direction y and a longitudinal centre line A as indicated. The article can be divided into a first and second mirror imaged longitudinal portions I and II, wherein the longitudinal portions are symmetrical in shape.

By the expression "symmetrical about the longitudinal centre line A" it is herein meant that each point in the article on first longitudinal portion I on a first side of the longitudinal centre line A has a corresponding point in the article on the second longitudinal portion II on the other side of the longitudinal centre line A; the two points being related to each other by reflection in a plane located on the longitudinal centre line A. For example a part of the first region 12 located on one side of the longitudinal centre line A is therefore the mirror image of the part of the first region 12 located on the other side of the longitudinal centre line A.

The total length of the article 1 in the longitudinal direction is length b, which is the sum of a length of the front portion b1, the crotch portion b2 and the rear portion b3 and sums up to 100% length of the article. The article 1 further has a front portion 2, a crotch portion 3 and a rear portion 4 arranged in the article's longitudinal direction as well as a transition 5 between the front portion 2 and the crotch portion 3. The article comprises an absorbent core 6.

In use, the front portion 2 of the article 1 is intended to cover the pubic region of a female wearer. The front portion 2 is delimited by the front transverse edge 27 of the article 1. Furthermore, the front portion 2 extends a certain length b1 along the article 1 in the longitudinal direction. In a sanitary napkin of the type shown, the front portion 2 has a length b1 in the longitudinal direction which is between 10-50%, more preferably between 10-40%, most preferably between 15-25% of the total length b of the article 1. The length can be for example between 30-70 mm, such as between 40-60 mm.

The crotch portion 3 of the article 1 is located adjacent to the front portion 2 in the longitudinal direction. In use, the crotch portion 3 lies between the legs of the user and covers a female user's genital region. In a sanitary napkin of the type shown, the crotch portion 3 has a length b2 in the longitudinal direction which is between 25-60%, more preferably between 30-55%, most preferably between 30-50% of the total length b of the article. Typically, the length b2 of the crotch portion 3 in the longitudinal direction y is between 60-150 mm, such as between 80-120 mm. The transition 5 between the front portion 2 and the crotch portion 3 is the border area between the front and crotch portions 2, 3.

The rear portion 4 is located at the opposite end of the article 1 from the front portion 2 and is located adjacent to the crotch portion 3 in the longitudinal direction. In use, the rear portion 4 extends towards the user's rear. The rear portion 4 is defined by the rear transverse edge 47 of the article 1 and extends a certain length b3 along the article 1 in the longitudinal direction, and is longitudinally distanced from a centre region 25 of an absorbent core 6. In a sanitary napkin of the type shown, the rear portion 4 has a length b3 in the longitudinal direction which is between 15-40%, more preferably between 20-35%, most preferably between 20-30% of the total length b of the article 1. The length b3 can be for example from 60 to 100 mm, such as between 70-90 mm.

The disposable hygiene article of the present disclosure comprises an absorbent core, which is indicated in the figures with reference sign 6. The "absorbent core" is the absorbent structure of the article which acquires and stores bodily fluids. The absorbent core may be of any conventional kind. Examples of commonly occurring absorbent materials are cellulosic fluff pulp, tissue, highly absorbent polymers (so called superabsorbents), absorbent foam materials, absorbent nonwoven materials or the like. It is common to combine cellulosic fluff pulp with superabsorbent polymers in an absorbent core. Superabsorbent polymers are water-swellable, water-insoluble organic or inorganic materials capable of absorbing at least about 20 times their own weight of an aqueous solution containing 0.9 weight percent of sodium chloride. Organic materials suitable for use as a superabsorbent material can include natural materials such as polysaccharides, polypeptides and the like, as well as synthetic materials such as synthetic hydrogel polymers. Such hydrogel polymers include, for example, alkali metal salts of polyacrylic acids, polyacrylamides, polyvinyl alcohol, polyacrylates, polyacrylamides, polyvinyl pyridines, and the like. Other suitable polymers include hydrolyzed acrylonitrile grafted starch, acrylic acid grafted starch, and isobutylene maleic anhydride copolymers and mixtures thereof. The hydrogel polymers are preferably lightly cross-linked to render the material substantially water insoluble. Preferred superabsorbent materials are further surface cross-linked so that the outer surface or shell of the superabsorbent particle, fibre, flake, sphere, etc. possesses a higher crosslink density than the inner portion of the superabsorbent. The superabsorbent materials may be in any form suitable for use in absorbent composites including particles, fibres, flakes, spheres, and the like. A high absorption capacity is provided by the use of high amounts of superabsorbent material. Thin absorbent cores which are common in for example sanitary napkins, baby diapers and incontinence guards, often comprise a compressed, mixed or layered structure of cellulosic fluff pulp and superabsorbent polymers. The size and absorbent capacity of the absorbent core may be varied to suit different product types, such as sanitary napkins for adult incontinent persons or panty liners.

Generally, the core can be of unitary construction, whereby for example the manufacturing process can be simplified. The phrase "unitary construction" in the present context is intended to mean that the absorbent core is constructed from essentially one type of material, this being essentially the same material, or essentially the same combination of two or more materials throughout the absorbent core. Variations in density and concentration of the material may occur, but these are limited to those which may be obtained without incorporation of regions which have been formed separately and then physically joined to each other. For example, when the absorbent core comprises a matrix of hydrophilic fibres and superabsorbent material as described above, the relative concentrations of superabsorbent material and fibres may be different in different parts of the core. However, the absorbent core of unitary construction does not comprise layers or laminates of different composition. Likewise, variations in the density or concentration of various components across the longitudinal direction, the transverse direction or the thickness direction of the absorbent core are acceptable, yet the core should not comprise areas or layers of different composition which are formed separately and later joined together. Examples of methods for production of the absorbent core will be described below.

As shown in FIGS. 1 to 6 and 8, an outer contour of the absorbent core 6 is defined by mirror-imaged first and second core edge lines 8, 9. The absorbent core 6 is delimited in the front portion 2 by a core front edge 7 and a core rear edge 57 in the rear portion 4. The outer contour defined by the core side edges differs in each of the front, crotch and rear portions 2, 3 and 4.

Figure 8:
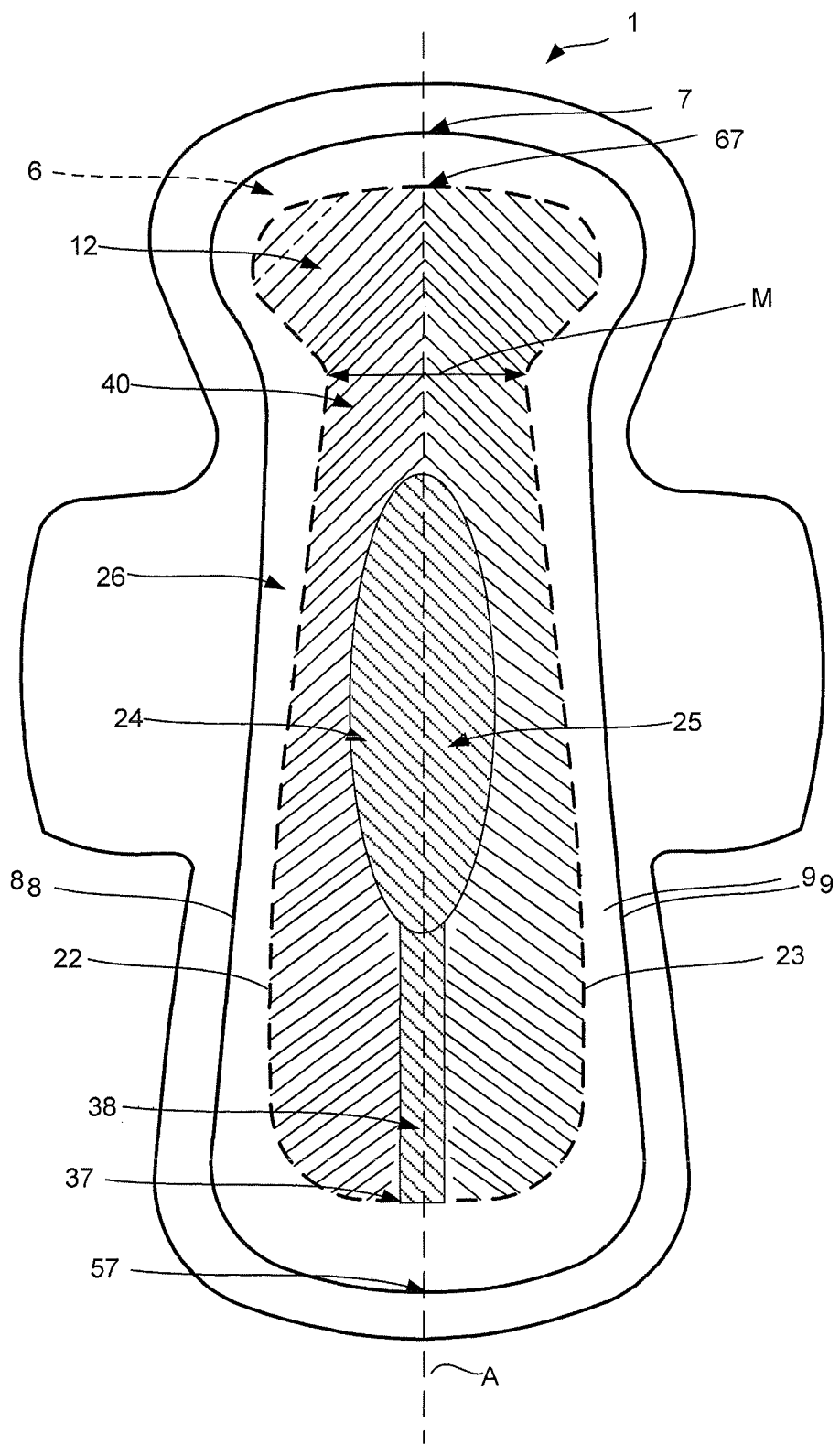
FIG. 8 shows schematically a plan view with highlighted first and second regions of a further example disposable hygiene article according to the present disclosure.

The absorbent core 6 comprises a first region 12, which is designed and arranged such that it is symmetric about the longitudinal centre line A of the article 1. This is important so that the article 1 lies symmetrically on the user's body when in use. The first region 12 may have the same outer contour as the absorbent core 6, as shown in FIGS. 1 to 6. Alternatively, the core 6 has a larger extension in both the transverse x and longitudinal y extension than the first region as shown in FIG. 8. In the embodiment shown in FIG. 8, the first region rear edge 37 is distanced from the core rear edge 57, and correspondingly, the first region front edge 67 is distanced from the core front edge 7. Similarly, the core edge lines 8, 9 are distanced from the first region edge lines 22, 23. In the embodiments shown in FIGS. 1 to 7, the first region edges 67, 37, 22, 23 correspond to the core edges 7, 57, 8 and 9, respectively.

The first region 12 comprises in the front portion 2 a head portion 13 and two leg portions 15, 16 extending symmetrically about a centre line A and in a longitudinal direction y of the article 1, starting from a start point $a_0$ in the crotch portion 3 and extending over a portion of the crotch portion 3 towards separate leg portion endings 17, 18 in the rear portion 4. The outer contour of the head portion 13 is defined by two mirror-imaged substantially convex lines in respect the longitudinal centre line A. The convex lines converge so as to define a "neck" for the first region 12, i.e. so as to define the narrowest width M in the transverse direction x for the first portion 12 between first and second first region edge lines 22, 23. The narrowest width M may be at the location of a transition 5, which is an area located between the front portion 2 and the crotch portion 3. Alternatively the narrowest width M is located in the front portion 2 and the transition 5 is located in the longitudinal direction between the narrowest width M and a transversal line crossing the start point $a_0$ for leg portions 15 and 16 of the core.

As shown in the drawings, the absorbent core 6 further comprises a second region 24. The leg portions 15 and 16 have facing sides 19, 20, which together with a first region rear edge 37 define an outer contour for a second region 24 of the core 6. The second region 24 comprises a centre region 25 and a rear section 38. There is a distance $a_x$ between the facing sides 19, 20 of the respective leg portions 15, 16 in the transverse direction x. The distance $a_x$ varies in the longitudinal direction y. A maximum distance $a_1$ between the facing sides 19, 20 of the respective leg portions 15, 16 in the transverse direction x is in the crotch portion 3. The maximum distance is suitably located at a position in the longitudinal direction y corresponding to a position of a crotch point 21. The "crotch point" is defined as a middle point of the centre region 25, which is located in a wetting area centrally in the crotch portion 3 of the article. The wetting area is the area where the liquid is initially expected to hit the article. In connection with articles adapted to absorb blood, such as sanitary napkins, it has been found that the crotch point should be located at the point being in contact with introitus. A longitudinal distance between a transversal line at the transition 5, which can correspond to a line drawn between two points at opposite edges of the core 6 at the point where the first region 12 has its narrowest width M, and the crotch point is about 63 mm when the user is sitting and about 67 mm when the user is standing, whereby an average distance of 65 mm can be calculated. This distance is indicated by reference sign $d_{CP}$ in FIGS. 1 and 2. The wetting area can then be defined as an area extending symmetrically from the crotch point 21 towards the edges of the article 1. For example, in case of a sanitary napkin, the wetting area includes the centre region 25 and extends from the crotch point 21 longitudinally about 3-4 cm towards the core front edge 7 and/or the core rear edge 57, respectively. Transversally, the wetting area may extend from side edge 8 to side edge 9 of the core 6, but may be narrower. For example, the wetting area may have an extension that substantially corresponds to the extension of the centre region 25. By providing a maximum width, i.e. a maximum distance between the leg portions 15, 16, of the centre region 25 at the point of the crotch point 21, improved liquid control in the wetting area can be provided.

The facing sides 19, 20 of the respective leg portions 15, 16 converge backwards in the longitudinal direction y such that said distance $a_x$ is reduced from the maximum distance $a_1$ to a minimum distance $a_2$.

The second region 24 is at least partially surrounded by the first region 12 and extends between the leg portions 15, 16 in the transverse direction x and in the longitudinal direction y from the leg portion start point $a_0$ in the crotch portion 3 to a longitudinal end point $a_1$ defining the extension of the leg portions 15, 16 in the rear portion 4. The leg start point $a_0$ is located in the centre line A so that a symmetrical leg shape can be provided in each longitudinal portion I and II. A distance $a_x$ between facing sides 19, 20 of the respective leg portions 15, 16 in the transverse direction x varies in the longitudinal direction y. In this way portions having different extensions in the transverse direction are provided to improve the fit and the absorbent properties in the article. The facing sides 19, 20 of the respective leg portions 15, 16 converge backwards towards the article rear edge 47 of the article in the longitudinal direction y such that said distance $a_x$ is reduced from said maximum distance $a_1$ to a minimum distance $a_2$. The minimum distance is preferably located outside the wetting area located in the crotch portion and is located in the rear portion 4 of the article 1.

The centre region 25 is located in the crotch portion 3, and a rear section 38 located in the rear portion 4 of the article 1. The first region is highlighted with stripes in FIGS. 6 and 8 and the second region 24 is surrounded by the first region 12, except in the first region rear edge 37 area of the core 6. The second region 24 suitably covers from 10-50%, such as from 20-40% of a total area of the core 6. The length of the second region 24 extending along the centre line A between the leg start point $a_0$ an end point $a_l$ in the rear portion 4 may vary greatly depending on the size of the article, but can be for example from 80 to 220 mm. The rear section 38 may have a length varying from for example 30-110 mm. The centre region 25 may have a length varying from for example 50-110 mm. The rear section 38 has a narrower width or extension in the transverse direction x than the centre region 25 or at least a portion of the centre region 25. The rear section 38 can have a lower average density of absorbent material than the centre region 25. Also the article in the rear section 38 has a lower stiffness than in the first region 12. Alternatively, the centre region 25 and the rear section 38 have substantially the same density. Thus, also the stiffness of the centre region 25 and the rear section 38 may be substantially the same.

Figure 9:
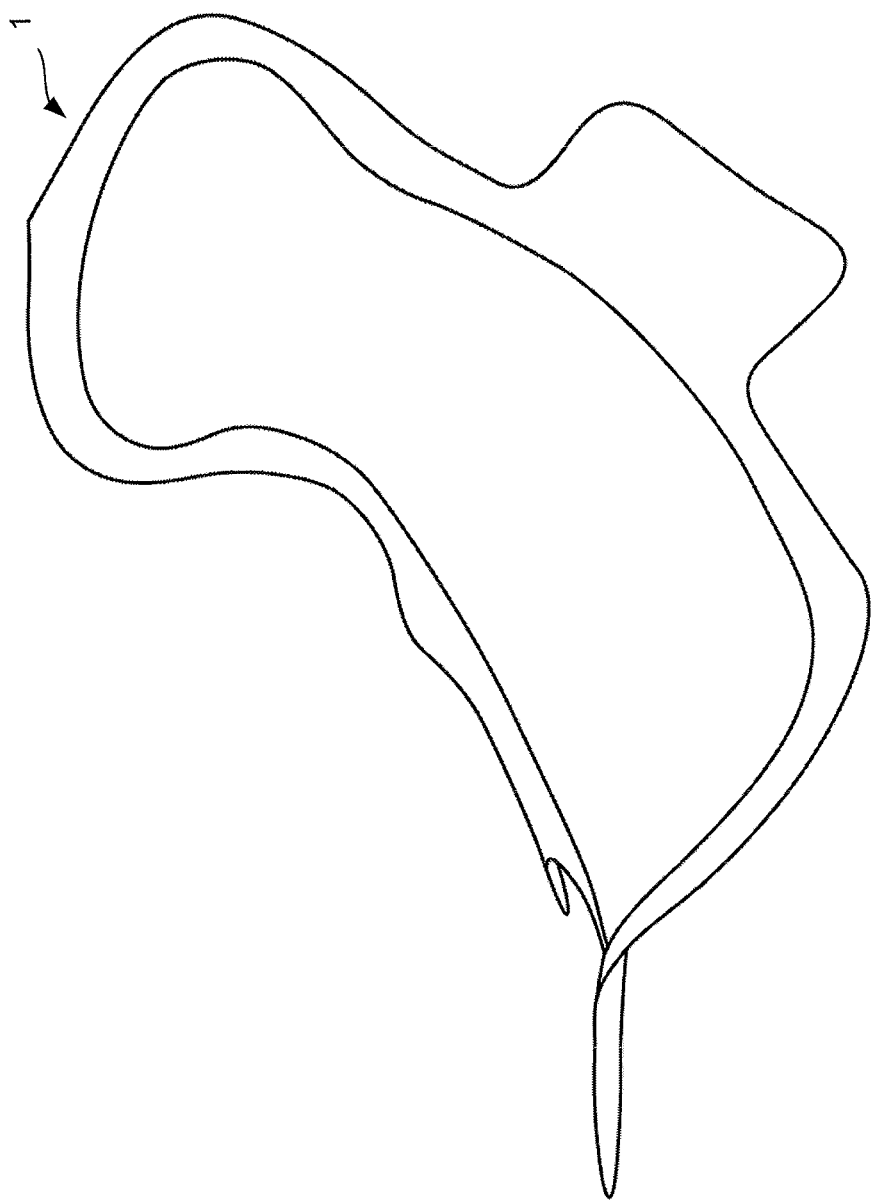
FIG. 9 shows schematically an article according to the present disclosure when in use, i.e. when bending forces are applied to the article during use.

Generally, the absorbent core has an asymmetrical shape in the longitudinal extension, but the first and second longitudinal portions are symmetrical in the transverse extension about the centre line A. The core may have different shapes, but the circumferential edges of the core define a shape in which a head portion and at least one neck area, i.e. an area with smaller width in the transverse direction, is located in the front portion or in the transition area of the core. In this way, the article can better conform to the body shape in the area where the front portion transitions to the crotch portion. Practically this means for example, that the article can bend in a transversal direction more easily in the area of the neck portion. Therefore, the front portion and the core head portion can bend towards the user and thus the front portion can better cover the pubic regions of the wearer while the crotch portion is able to locate close to the genital area of a female wearer. In this way, the article is easily held in a correct position during use. FIG. 9 illustrates how the product bends in use.

Generally, as described above, the core has a unitary construction produced in a one-step process of a common core material. By the first region and the second region are meant regions of the core having different properties, i.e. the density is different and the areas may be embossed and/or printed with different designs and the first region is stiffer than the second region. In this way the first and second regions may be differentiated by means of different physical properties and visually. By different properties in the regions, the fit of the product may be improved and/or the positioning of the product e.g. on the user's underwear can be facilitated.

FIGS. 1, 2, 3, 4 and 5 show examples of embodiments of the disposable hygiene article according to the present disclosure. In the figures, a disposable hygiene article 1 comprising a core 6 with the first region 12 and the second region 24 as basically described above is shown. The core 6 comprises in the lower part of the crotch portion 3, i.e. the part closest to the rear portion 4, a first rear compression line 61 and a second rear compression line 63.

Figure 3:
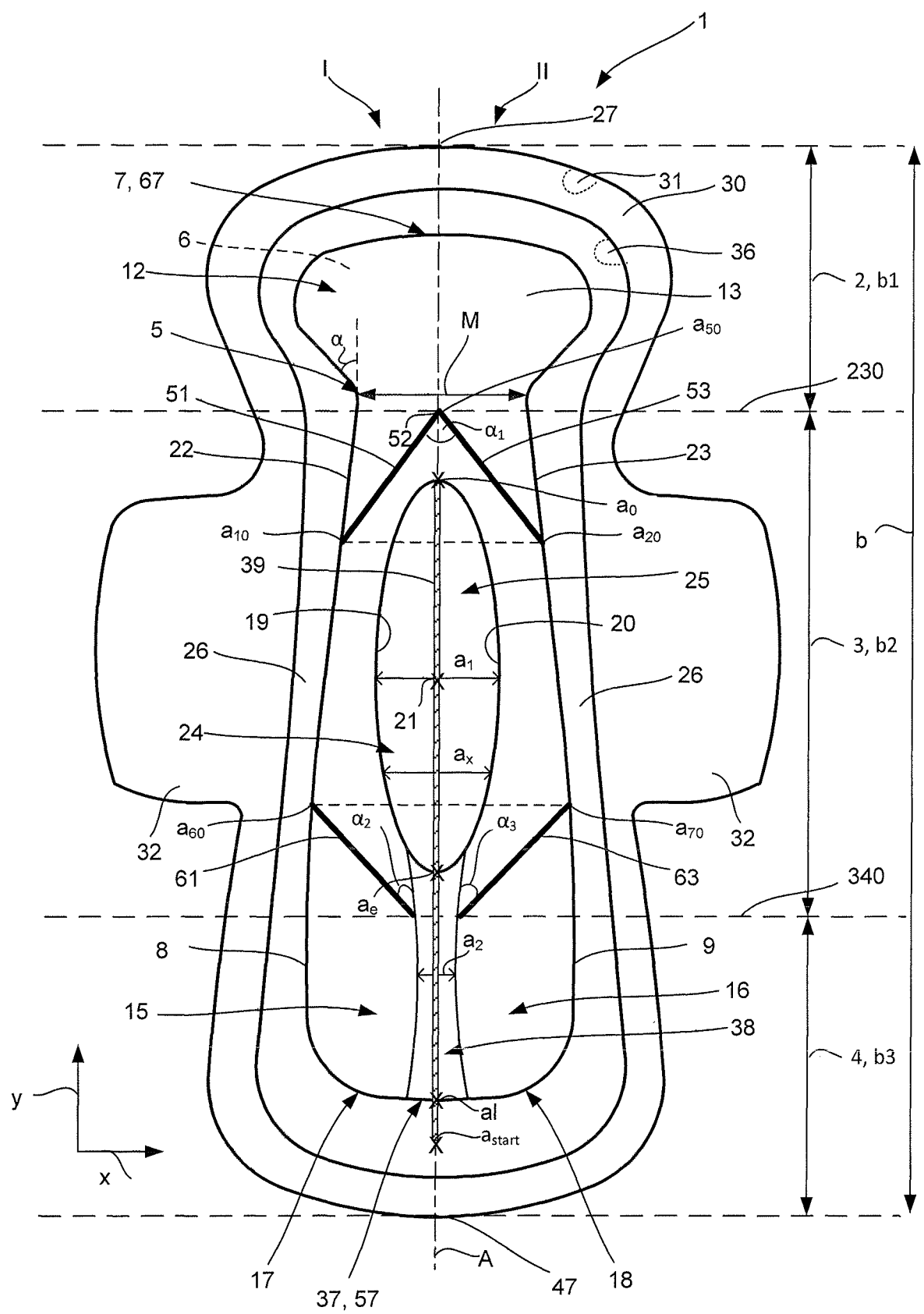
FIG. 3 shows schematically a plan view of another example disposable hygiene article according to the present disclosure.
Figure 5:
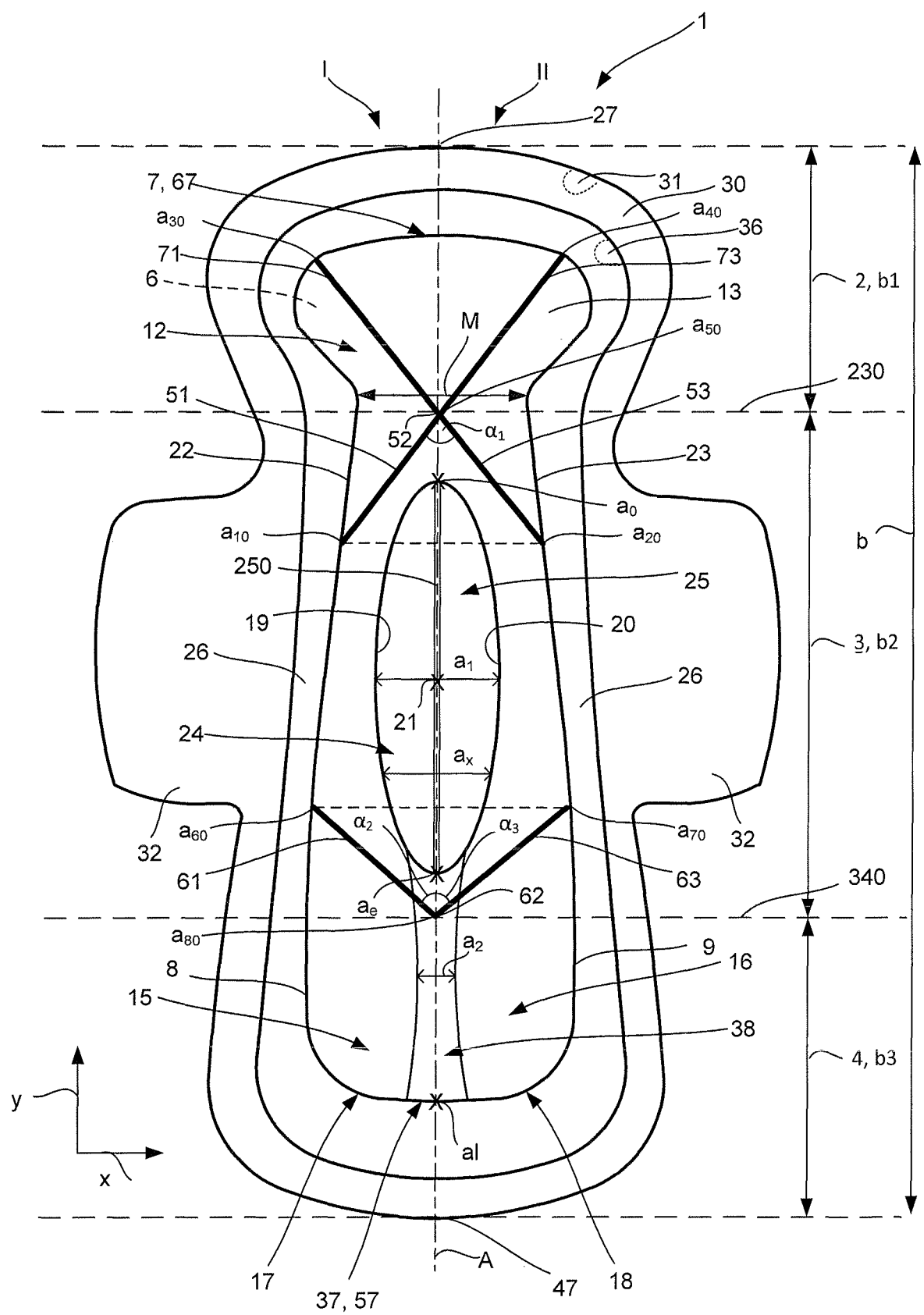
FIG. 5 shows schematically a plan view of a further example of a disposable hygiene article according to the present disclosure.

According to embodiments shown in FIGS. 1, 3 and 5, the first and second rear compression lines 61, 63 form an essentially V-shaped compression line comprising a common rear tip 62 in which the lines 61, 63 meet. The rear tip 62 has an imaginary contact point $a_{80}$ with an imaginary rear division line 340 dividing the article 1 into the crotch portion 3 and the rear portion 4.

Figure 2:
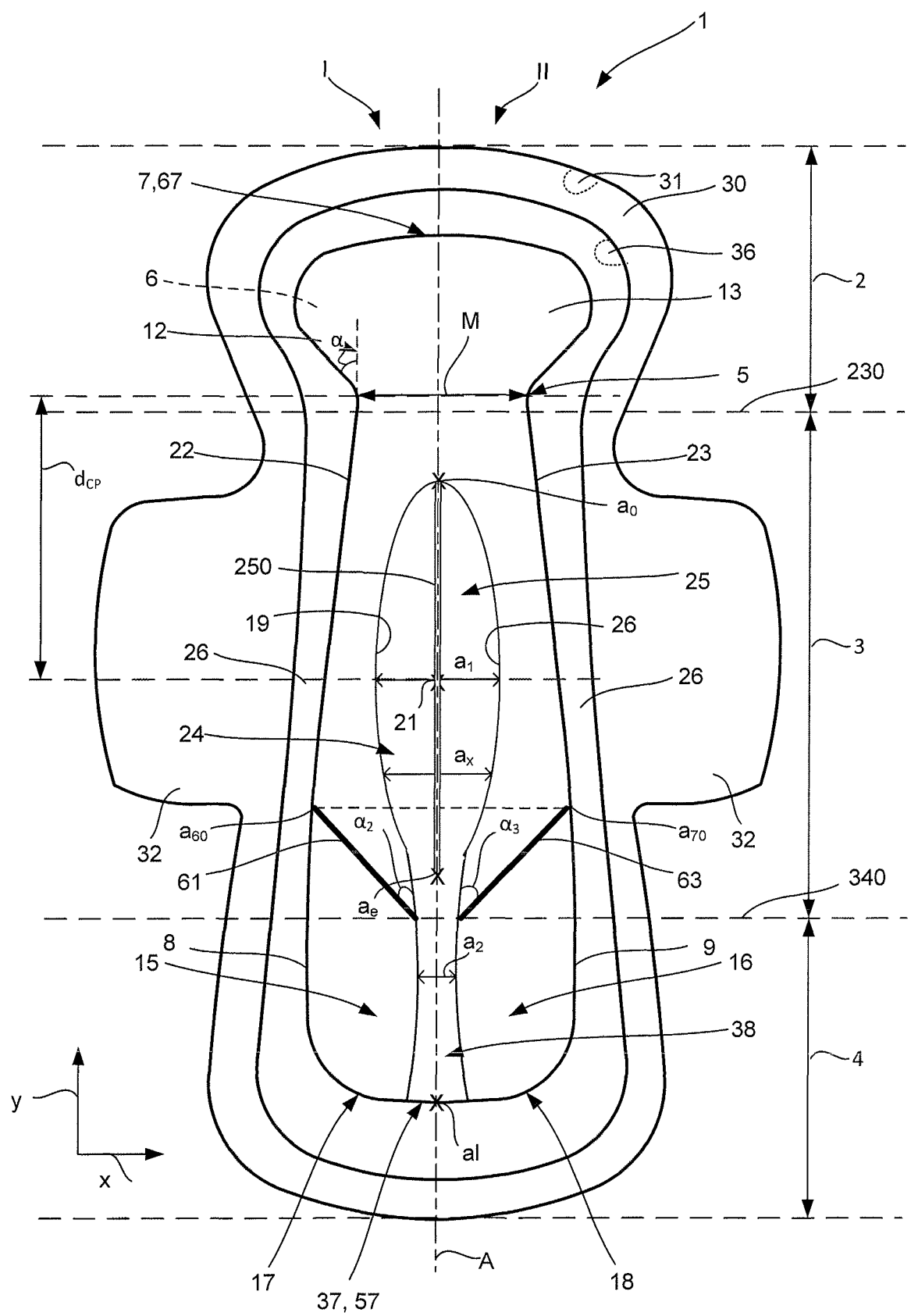
FIG. 2 shows schematically a plan view of another example disposable hygiene article according to the present disclosure.
Figure 4:
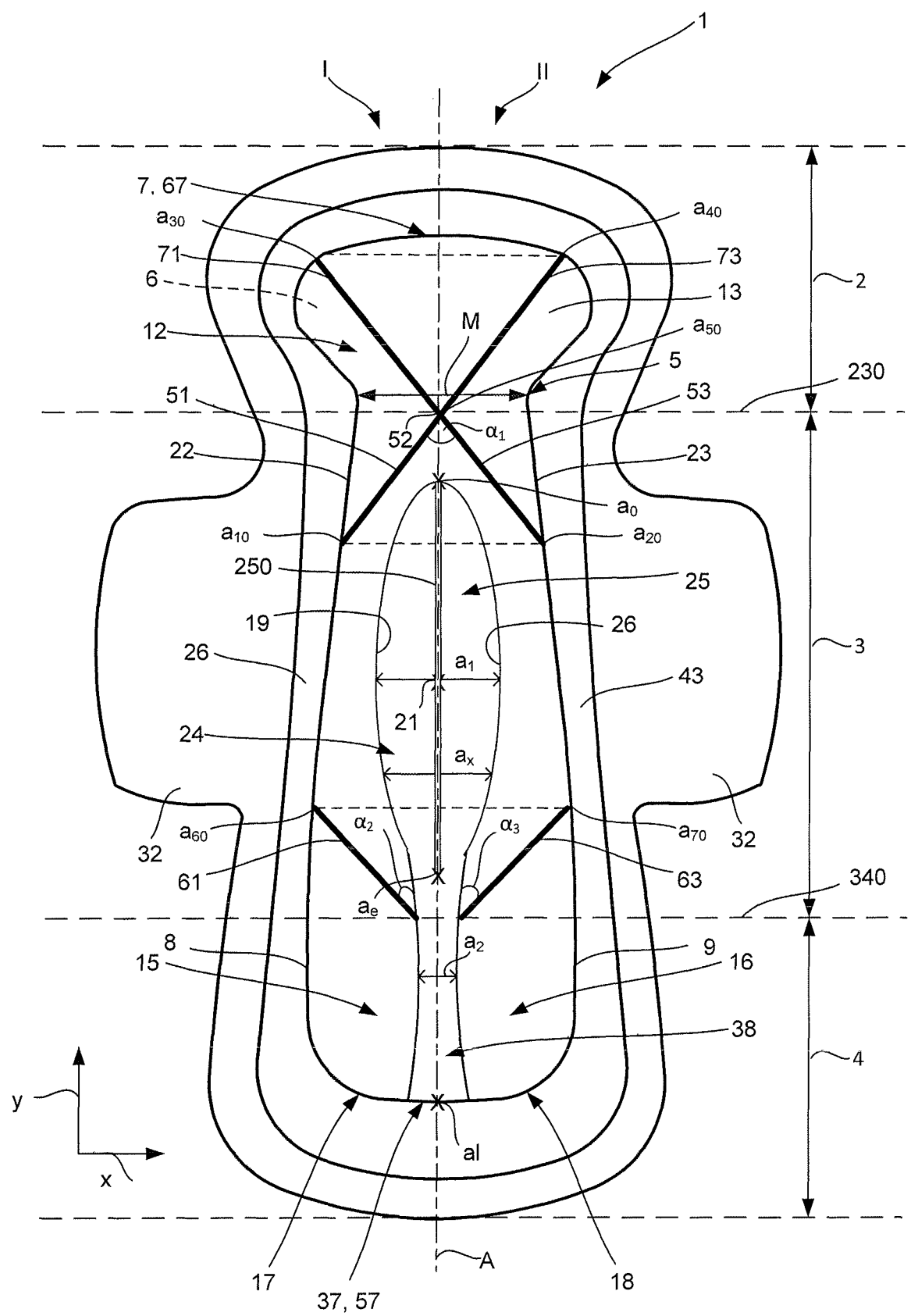
FIG. 4 shows schematically a plan view of a further example of a disposable hygiene article according to the present disclosure.

FIGS. 2 and 4 show another embodiment of the rear compression line according to the present disclosure. In this embodiment the first and second rear compression lines 61, 63 are distanced from each other in transverse direction x and thus free from a common rear tip. In the embodiment of FIG. 2, the compression lines 61 and 63 start from the respective facing side 19, 20 delimiting the rear section 38, and extend along the first region 12 of the core 6. The first and second rear compression lines 61, 63 mutually diverge in a direction towards the core front edge 7 and the first region front edge 67. The lines have suitably an imaginary contact point with an imaginary rear division line 340 dividing the article 1 into the crotch portion 3 and the rear portion 4. The lines 61, 63 further promote transversal bending of the rear portion towards the body of the user during use, and thus further improve fit and how the article conforms to the body of the user.

In all the embodiments, the rear compression lines are substantially straight. The first rear compression line 61 has a diverging angle $\alpha_2$ from 15-60°, suitably 30-45°, in respect of the extension of the centre line A. The second rear compression line 63 has the same, but mirror imaged diverging angle $\alpha_3$ as the angle $\alpha_2$, and is also of from 15-60°, suitably 30-45°, in respect of the extension of the centre line A. The first rear compression line 61 has an extension up to the respective first region edge line 22 and the second rear compression line 63 has an extension to the respective second first region edge line 23. The first rear compression line 61 contacts the first region edge line 22 at a first rear contact point $a_{60}$ and the second rear compression line contacts the second first region edge line 23 at a second rear contact point $a_{70}$. If the core 6 has a larger extension than the first region 12, the first and second rear compression lines can extend up to the respective first and second core edge lines 8, 9.

In FIGS. 3, 4 and 5 are shown embodiments in which the absorbent article comprises in the first region 12, which forms an essentially upside down turned V comprising a first leg 51, a second leg 53 and a common front tip 52. The tip 52 is located on the centre line A and has an imaginary contact point with an imaginary line 230 dividing the article 1 into the front portion 2 and the crotch portion 3. The first and second legs 51 and 53 diverge towards the first region rear edge 37 at a mutual angle $\alpha_1$ of from 30-120°, suitably from 45° to 100°, and extend up to the respective the first and second first region edge lines 22, 23. The first leg 51 has a first leg ending point $a_{10}$ on the first region edge line 22, and the second leg 53 has a second leg ending point $a_{20}$ on the second first region edge line 23. Alternatively, the legs 51, 53 could extend up to the core edge lines 8 and 9. An imaginary line drawn between the first and second leg ending points $a_{10}$ and $a_{20}$ preferably extends in the transversal direction x. The common tip 52 having an imaginary contact point with an imaginary front division line 230 is located in contact with or at small distance in proximity of an imaginary transverse line indicating the narrowest width M of the first region 12. The distance may be from 0 to 10 mm. The location of the front tip 52 in that manner promotes the transversal bending of the article along the front division line 230 in a synergetic manner. The front division line 230 corresponds to the transition 5, i.e. an area dividing the article to a front portion and crotch portion.

In case the transition 5 or transition area corresponds to the area of the first region 12 in which the first region has the narrowest width M, the transition 5 between transverse and longitudinal edges is defined as the point on the edge of the first region at which the rate of curvature of the transverse edge of the first region with respect to the transverse direction is greatest. The first region 12 may alternatively have its narrowest width M in the transverse direction x in the front portion 2. This means that the location of transition 5 between the front portion 2 and the crotch portion 3 can be positioned at the point of the common tip 52 and thus can be longitudinally distanced from the narrowest width M in the transverse direction x towards the core rear edge 57 of the first region 12 by e.g. 0-10 mm. In the transition area, the transition between transverse and longitudinal edges can be defined as the point on the edge of the core at which the rate of curvature of the transverse edge of the core with respect to the transverse direction is greatest.

The longitudinal first region edges 22, 23 of the core can be in the crotch portion 3 and the rear portion 4 substantially parallel or may diverge towards the rear edge of the article. The angle of the longitudinal edge diverging in respect to the centre line A may suitably be from 0-10°, preferably 0.5-2°.

The average density of the second region 24 in the absorbent core 6 is lower than the average density of the first region 12 in the absorbent core 6. Thus, the absorbent core 6 is stiffer in at least a portion or the whole first region 12 than the second region 24 of the absorbent core 6. Generally by stiffness is meant the extent of a material to resists deformation in response to an applied force. The absorbent articles are mainly subjected to bending forces applied by the user's body and clothing and stiffer portions of the core are better able to withstand bending forces than the portions having lower stiffness. By providing higher average density and thus stiffer first region 12 than the second region 24 of the core 6 which is located centrally and extends along the centre line A, the article can conform to the shape of the body while the first region better retains the original shape and thus provides robustness in shape retaining of the article during the use. Thus, the first region 12 can better withstand bending forces than the second region 24 having a lower stiffness. Therefore, for example the risk for deformation of the shape and thus for example movement 0.7 of the article during use is minimized.

Further, in the embodiments shown in FIGS. 4 and 5, the core 6 and the first region 12 thereof further comprises an additional V-shaped front compression line which comprises a third leg 71 and a fourth leg 73 which each extends and diverges towards the core front edge 7 and the first region front edge 67 from the common front tip 52 in the respective mirror-imaged portions (I) and (II). The third leg 71 and the fourth leg 73 diverge at a mutual angle $\alpha_4$ of from 30-120°, suitably from 45° to 100°, and extend up to the respective the first and second first region edge lines 22, 23 or to the respective core edge lines 8, 9. The third leg 71 has a third leg ending point $a_{30}$ on the first region edge line 22, and the fourth leg 73 has a fourth leg ending point $a_{40}$ on the second first region edge line 23. A line extending between the third and fourth leg ending points $a_{30}$ and $a_{40}$ preferably extends in the transversal direction x. The legs 51, 53, 71 and 73 with the common tip 52 thus together form an X-shaped compression line. Preferably, the angles $\alpha_1$ and $\alpha_4$ are equal, but minor differences are possible and thus the difference is suitably from 0-10°. Alternatively, the embodiments of FIGS. 2 and 3 do not need to comprise the additional V-shaped front compression line which comprises a third leg 71 and a fourth leg 73. Further, it would be possible to add the additional V-shaped front compression line which comprises a third leg 71 and a fourth leg 73 to the embodiment shown in FIG. 1.

By essentially upside down turned V-shape or V-shape is meant that the shape is symmetrical in respect to the centre line A or that the upside down turned V-shape or V-shape is slightly inclined in respect to the centre line A, e.g. due to manufacturing tolerances. The lines forming the V-shape are substantially straight, i.e. not curved. Thus, a respective leg in respective longitudinal portion I and II may have a different angle of inclination in respect to the centre line A. For example, when the shape of the upside down turned V is symmetrical a line between the ending points $a_{10}$ and $a_{20}$ is transversal and not essentially inclined in respect to the transversal direction x. In a similar manner the line between the ending points $a_{60}$ and $a_{70}$, and the ending points $a_{30}$ and $a_{40}$ is transversal. However, minor inclination is possible, but the inclination of the line extending between the ending points should be less than 5°, i.e. 0-5°, meaning that the inclination of the line between the ending points $a_{10}$ and $a_{20}$ in respect of the transversal extension x should be less than 5°. Also, the length of the respective legs in respective longitudinal portion may be different. The length difference should be at most 10%. For example, if the length of the leg in the first longitudinal portion I is 40 mm, the length of the leg in the second longitudinal portion should be within a range from 36 to 44 mm.

The rear and the front compression lines 61, 63, 51, 53, 71 and 73 may be provided by means of groove or line compressing the core 6 and optionally the liquid acquisition sheet 36 and/or the topsheet with high pressure compression from the topsheet 30 or the backsheet 31 side of the article. The backsheet of the article can be retained unacted and thus the liquid impermeability of the backsheet is not affected. The front compression line is located in contact with or in proximity of the imaginary transversal line M indicating the narrowest width of the core, and the location of the smallest width M is distanced from the common front tip 52 in a longitudinal direction y by 0-10 mm. In this way, a further promoted transversal bending of the front portion 2 towards the user, and thus the formation of a bowl shape shown in FIG. 9 is obtained.

The second region 24 which comprises the centre region 25 extending symmetrically about the centre line A, has a longer extension in the longitudinal direction y than in the transverse direction x. Suitably, the centre region 25 has an oval shape or a shape of a parallelogram with edges being located along the centre line A and thus the centre region 25 extends longitudinally and symmetrically about the centre line A. The second portion 24 further comprises a longitudinally and symmetrically about the centre line A extending rear section 38. The rear section 38 is in contact with the centre region 25 and can overlap with the centre region 25. Further, the rear section 38 is limited by the facing sides 19, 20 of the respective leg portions 15, 16 and the first region rear edge 37.

As shown in FIGS. 1, 2 and 4, the centre region 25 may comprise a weakening compression line 250 extending along the centre line A between a start point $a_0$ and a centre region end point $a_e$. Such weakening compression line 250 may be present in all the embodiments of the present disclosure and is not limited to the one shown in FIGS. 1, 2 and 4. The centre region end point $a_e$ is a point that corresponds to a point in the centre line A where the shape defining the centre region ends or just below the end point. In this way lower resistance towards mechanical strength bending the article can be provided, i.e. when forces from the thighs of a user act on the sides of the article in the centre region 25. Thus the centre region can bend along the centre line A towards the body of the user in an easier way. Therefore, the feeling of security against leakage can be improved. The weakening compression line 250 can be embossed from the side of the core facing the backsheet 31, whereby the centre region 25 bends towards the body of the user.

The absorbent article according to the present disclosure may further include a liquid acquisition sheet, which acts as a liquid distribution layer. The liquid acquisition sheet is located between the topsheet and the core and is suitably placed on top of the absorbent core. In FIG. 1 the liquid acquisition sheet is shown with reference sign 36. The liquid acquisition sheet is adapted to quickly receive and temporarily store discharged liquid before it is absorbed by the absorbent core. Such acquisition distribution layers may be composed of for example airlaid nonwoven, spunlace nonwoven, high loft nonwoven or foam materials. The nonwoven material may be hydrophilic. A hydrophilic material may be obtained by adding a surfactant.

An air laid nonwoven can be produced with fluff, wood pulp, and here the fluff fibres are dispersed into a fast-moving air stream and condensed onto a moving screen by means of pressure and vacuum. The web can be bonded with resin and/or thermal plastic resin dispersed within the pulp. The web can be thermobonded (by heat), latex bonded (with adhesive) or multibonded (a combination of thermo and latex bonding) or mechanically bonded (high compression and temperature, bonding by hydrogen). The grammage of the airlaid nonwoven can suitably be from 50 to 100 gsm.

High loft is a nonwoven material and may be substantially free from absorbing fibres and superabsorbent material. The high loft nonwoven material may comprise thermoplastic polymer fibres, and may be selected from but not limited to, polyesters, polyamides and polyolefins such as polyethylenes (PE) and polypropylenes (PP), and may be a mixture of any of these. The "high loft" refers to low density bulky fabrics, as compared to flat, paper-like fabrics. High loft webs are characterized by a relatively low density. This means that there is a relatively high amount of void space between the fibres. The high loft nonwoven fibrous layer of the invention may typically have a density below 0.200 g/cc (200 kg/m$^3$), in particular ranging from 0.015 g/cc to 0.150 g/cc (15 kg/m$^3$ to 150 kg/m$^3$), in particular from 0.030 g/cc to 0.100 g/cc (30 to 100 kg/m$^3$), for example 0.065 g/cc (65 kg/m$^3$).

The average density can be calculated by dividing the basis weight of the high loft layer by its thickness measured at a pressure of 0.5 kPa (see the method details further below). Normally the thickness of high loft materials is more than about 0.5 mm, such as more than 1 mm or suitably 1.5-2.0 mm, and the solid content is low, usually less than 15% by volume. The high loft nonwoven layer may advantageously be a spunmelt nonwoven. Spunmelt is a generic term describing the manufacturing of nonwoven webs directly from thermoplastic polymers. It encompasses 2 processes and the combination of both: spunlaid (also known as spunbond) nonwoven and meltblown nonwoven. In a spunlaid process, polymer granules are melted and molten polymer is extruded through spinnerets. The continuous filaments are cooled and deposited on to a conveyor to form a uniform web. Some remaining temperature can cause filaments to adhere to one another, but this cannot be regarded as the principal method of bonding. The spunlaid process has the advantage of giving nonwovens greater strength, but raw material flexibility is more restricted. Co-extrusion of second components is used in several spunlaid processes, usually to provide extra properties or bonding capabilities. In meltblown web formation, low viscosity polymers are extruded into a high velocity airstream on leaving the spinneret. This scatters the melt, solidifies it and breaks it up into a fibrous web. The liquid acquisition sheet material may be of a spunbonded material and may be a spunbond-meltbond-spunbond (SMS) material. The high loft nonwoven layer may in particular have a thickness ranging from 0.30 mm to 2.00 mm, for example 1.0 mm as measured at a pressure of 0.5 kPa (according to the test method described further below). The grammage, i.e. basis weight of the high loft material may for example range from 15 gsm to 500 gsm, in particular from 30 gsm to 200 gsm, such as 30-90 gsm, for example 64 gsm.

According to a further variant, the acquisition sheet is a spunlace, also referred to as spunbond, nonwoven material. A spunlace nonwoven product is derived from a process of entangling a web of loose fibres through multiple rows of jets of water at high pressure; this process entangles the fabrics and interlinks the fibres. There are several terms for spunlace nonwoven fabric or spunlaced, such as jet entangled, needled, hydroenentangled or hydraulic, but the term spunlace or spunlaced is the most popular in the nonwoven industry. The raw material for the acquisition sheet can be polypropylene (PP), polyethylene (PE) polyester (PET), polyamide (PA), cellulosic fibres or a combination of these and different weights and compositions are possible, such as viscose, polyester, cotton, nylon and microfibre, wherein viscose is the most commonly used raw material. Thus, if a combination of different fibres is used, this can be a mixture of fibres from different polymers, although each fibre can also include different polymers (e.g. PP/PE bi-component fibres or PP/PE copolymers). Where appropriate, in certain embodiments, the plastic film may consist of or may comprise PE or PP, PET, PLA or amyl (or, for that matter, any other thermoplastic polymer), or a mixture or copolymers of the aforementioned polymers. The spunlace material usually comprises polypropylene or polyethylene fibres which provide for optimal comfort for the nonwoven material. Other suitable fibres for making the nonwoven material are for example natural fibres such as bamboo, cotton and flax. The grammage of the spunlace nonwoven material can be typically from 40-90 gsm.

According to the present disclosure the liquid acquisition sheet 36 may have a larger extension in both the transverse x and longitudinal extension y of the core 6 as shown in FIGS. 1 to 6. In this way it is possible to obtain soft side edge areas. This means that the core is completely covered by the liquid acquisition sheet. Leakage control may be improved, especially in the areas where the core 6 has a narrow extension in the transversal direction x, such as in an area of transition 5 which will be explained more in detail below. Leakage control can be obtained since the liquid acquisition sheet is able to trap at least a part of e.g. menstrual fluid in the areas outside the core whereby the fluid will thus not leak outside the hygiene article.

FIG. 7 shows another example of a disposable hygiene article according to the present disclosure is shown. The article 1 comprises a core 6 with a compressed first region 12 having a higher stiffness and density than the second region 24. The first region 12 surrounds at least partially the second region 24. The second region comprises the centre region 25 and the rear section 38. The core 6 has the same extension as the liquid acquisition sheet 36. An edge area 26 surrounds the first region 12 and is suitably less compressed than the first region 12. The edge area 26 can have essentially the same physical properties, i.e. for example density and stiffness, as the second region 24. Alternatively, the density in the edge areas 26 can be lower than in the centre region 25 and/or rear section 38.

As explained previously in connection with FIGS. 1 to 6, the first region 12 is comprised in the front portion 2, the crotch portion 3 and the rear portion 4. The first region 12 comprises two leg portions 15, 16 extending in the longitudinal direction y of the article 1 from the start point $a_0$ in the crotch portion 3, over the remainder of the crotch portion 3 towards separate leg endings 17, 18 in the rear portion 4. Thus, the two leg portion 15, 16 extend over a considerable part of the crotch portion 3 towards the separate leg portion endings 17, 18 and are arranged symmetrically about the longitudinal centre line A of the article 1. Furthermore, each leg portion 15, 16 has a side 19, 20, i.e. an edge, facing the other leg portion 15, 16. The distance $a_x$ between the facing sides 19, 20 of the respective leg portions 15, 16 in the transverse direction x of the absorbent article 1 vary along the longitudinal direction y of the article 1 in the crotch portion 3 and may vary also in the rear portion 4. That is, the edges of the respective leg portions 15, 16 lying closest to the longitudinal centre line A, i.e. the facing sides 19, 20, are not parallel with the longitudinal centre line A. The distance $a_x$ therefore exhibits maxima and minima along the longitudinal direction of the article 1. According to one variant, the distance $a_x$ varies continuously along the longitudinal direction of the article 1. Thus, as shown in FIGS. 1-6 and 8, the facing sides 19, 20 of the respective leg portions 15, 16 converge backwards in the longitudinal direction of the article 1 such that the distance $a_x$ between the facing sides 19, 20 of the respective leg portions 15, 16 in the transverse direction x is reduced from the maximum distance $a_1$ in the crotch portion 3 to a minimum distance $a_2$ in the rear section 38. In other words, the facing sides 19, 20 of the respective leg portions 15, 16 converge in a backward direction of the article 1 from the position in the longitudinal direction where the maximum distance $a_1$ is located to the position in the longitudinal direction where the minimum distance $a_2$ of the rear portion 4 is located. According to another variant shown in FIG. 8, in the rear section 38 the facing sides 19, 20 may have a constant distance which suitably corresponds to the minimum distance $a_2$, which means that the facing sides 19, 20 are parallel in the rear section 38. For example, the minimum distance $a_2$ in the rear section 38 may be 5-30 mm, more preferably 10-20 mm, most preferably 10-15 mm.

The facing sides 19, 20 of the respective leg portions 15, 16 also converge forwards in the longitudinal direction such that the distance $a_x$ between the facing sides 19, 20 of the respective leg portions 15, 16 is reduced from the maximum distance $a_1$ in the crotch portion 3 to a zero distance in the crotch portion 3. In other words, the facing sides 19, 20 of the respective leg portions 15, 16 converge in a forward direction of the article 1 from the position in the longitudinal direction where the maximum distance $a_1$ is located to a position in the longitudinal direction where the two facing sides 19, 20 meet at the point $a_0$. Thus, the two facing sides 19, 20 of the respective leg portions 15, 16 are joined in the crotch portion 3. The position where the two facing sides 19, 20 are joined is denoted as the leg start point $a_0$. The facing sides 19, 20 of the two leg portions 15, 16 are joined in the crotch portion 3 and the first region 12 does not comprise any leg portions in the transition 5 nor in the front portion 2. In this way it can be assured that the article will conform to the body of the user in an efficient way.

Furthermore, the first region 12 has a width M in the transverse direction at the transition 5 between the front portion 2 and the crotch portion 3 or in the front portion 2. The width M is adapted to the distance between two particular muscle tendons on both sides of the crotch of the wearer directly in front of the groins. These muscle tendons form part of the muscle group which originates on the inside of the pelvic diaphragm and has its attachment along the thigh. This muscle group consists of the adductor muscles, adductor longus, gracilis and adductor magnus muscles. It is known that the distance between said two muscle tendons, is very similar for all people: around 25-45 mm. Research has shown that 80% of all women have a dimension of 30-32 mm between said muscle tendons. The term "transition between the front portion and the crotch portion" is herein intended to mean the region which in the intended use of the article 1 is located between the two mentioned muscle tendons.

The width M of the first area, which has a higher density than the second area and is thus stiffer than the second region, is preferably between 15 and 45 mm, more preferably between 25 and 35 mm. If the width M exceeds about 35 mm, the article 1 is likely to feel uncomfortable for the majority of wearers. When said width M essentially corresponds to the distance between said muscle tendons on the wearer, and in case the article is positioned with the transition portion between the muscle tendons, the article will be less likely to move from its position.

The two side edges 22, 23 of the first region in the front portion 3 diverge in the forward direction on the product from the transition 5. An angle between a line in the longitudinal direction of the article 1 and each of the side edges 22, 23 of the head part 13 has been designated by a in FIG. 3.

The angle α is measured where the angle between a line in the longitudinal direction of the article 1 and each of the side edges 22, 23 is largest. In the case of a large angle α, for example close to 90°, the side edges 22, 23 in the front portion 2 may chafe against the groins and the legs of the wearer and in this way cause discomfort for the wearer. The smaller the angle α, the greater the risk that the article 1 will slide backwards in between the legs of the wearer. In the case of an angle α of less than 30°, this risk is unacceptably high. An angle α of 40-70° provides the best balance between secure positioning and comfort. An angle α of 45-65° has been found to be especially favorable. In this way, the product is prevented from moving backwards between the legs of the wearer. This is a common problem in conventional sanitary towels because the leg movements of the wearer often shift the sanitary towel backwards. Due to the stiffness of the core 6 in the first region 12 at the width area M, the core will not fold. If the width M exceeds 45 mm, discomfort and chafing is highly likely to occur due to the higher stiffness of the first region 12.

As explained above, the second region 24 is surrounded by the first region 12 is further constituted by the centre region 25 extending between the facing sides 19, 20 of the leg portions 15, 16 and the rear section 38. The width of the rear section in the transverse direction x is preferably >5 mm, more preferably 5-20 mm, in an orthogonal direction from said circumferential edge 7. According to the present disclosure, the absorbent core 6 has a lower average density in the second region 24 than in the first region 12. That is, the average density of the absorbent core 6 in the second region 24 is lower than the average density of the absorbent core 6 in the first region 12. Preferably, the second region 24 has a lowest density which is at least 20% lower, more preferably at least 30% lower and most preferably at least 50% lower than the density of the first region 12. Furthermore, the average density within each of the first region 12, the centre region 25 and the rear section 38 may vary or be constant. The average density of the centre region 25 and the rear section 38 may be the same or different, but each has always lower average density than the first region. The second region can have up to 70% lower density than the first region 12. For example, if the absorbent material of the core is fluff pulp, the density of the fluff pulp in the first region 12 is preferably 150-220 kg/m$^3$, more preferably 160-220 kg/m$^3$, and the average density of the fluff pulp in the second region 24 is preferably 70-150 kg/m$^3$, more preferably 80-130 kg/m$^3$. The exemplified density ranges for the first region 12 and the second region 24 imply that the first region 12 and the second region 24 are provided with different stiffness. If another absorbent material than fluff pulp is utilized for the core 6, the same different stiffness of the first region 12 and the second region 24 may be provided by other densities of the first and second regions 12, 24.

Suitably, the thickness of the centre region 25 is greater than the thickness of the first region 12. The density of the rear section 38 may be equal to or lower than the density of the first region 12. Also, the thickness of the rear section 38 may be lower than the thickness of the centre region 25 or may be the same. The average density of the respective area may be calculated from the grammage and the thickness of the respective areas and is further described below.

Furthermore, if the absorbent material comprises a superabsorbent polymer (SAP), the weight and volume of SAP are omitted when the density of the first and second regions 12, 24 is calculated in the context of the present invention. This is due to the fact that SAP particles or granolas have a relatively high average polymer-density.

As above mentioned, the second region 24 is divided into a centre region 25 and a rear section 38. The average density of the centre region 25 and the rear section 38 may be the same or different. Furthermore, the average density within each of the first region 12, the centre region 25 and the rear section 38 may vary or be constant.

Suitably, the thickness of the centre region 25 is greater than the thickness of the first region 12. However, the thickness of the core may be uniform in case of a large core, i.e. a core which extends longitudinally and transversally outside the first region edge lines. The density of the rear section 38 may be equal to or lower than the density of the first region 12. Also, the thickness of the rear section 38 may be lower than the thickness of the centre region 25 or may be the same. The average density of the respective area may be calculated from the grammage and the thickness of the respective areas and is further described below.

Material should be present in the lower average density regions 25, 38—the situation in which the average density of the lower density regions 25, 38 is zero is not comprised within the scope of this invention.

A number of methods for measuring the average density of absorbent cores, or the average density of samples, have been described in the literature. In particular, the average density of a sample of absorbent core may be measured according to the following procedure:

The absorbent article is carefully delaminated: any inner or backsheets are removed so as to only leave a unitary core.

A pressure of 0.5 kPa is applied to the absorbent core via a foot which is smaller than the area of the sample of an absorbent core for which the density is to be measured, so that the foot is placed inside the area to be measured.

The thickness of the sample is measured while subject to this pressure.

The samples for which densities are to be calculated are cut out from the core, and the surface weight (g/cm²) of these samples is calculated from their mass/surface area.

From the surface weight and the thickness, the average density of these areas is calculated. The average density (kg/m³) is calculated by dividing the surface weight by the thickness.

The geometrical design of the first region 12 and the average density difference and the stiffness difference, between the first and second regions 12, 24 promote formation of an advantageous 3-dimensional form of the article 1 when it is used. FIGS. 6 and 8 schematically shows the regions in the article. The advantageous 3-dimensional form provides a very good anatomical adaptation of the article 1, i.e. a good fit of the article 1 is provided. In addition, stability of the article 1 in the fitted position on the wearer is provided. Stability of the article 1 is provided, for example, by the high average density of the first region 12. The density difference may be obtained by mean of compression. Alternatively or additionally, the density difference may be provided or promoted by means of providing an embossing pattern to the first region. The embossing pattern is suitably visible from the side of the top sheet of the article. Preferably, the first region 12 comprises a discontinuous embossing pattern 40 which covers said first region and wherein the second region 24 is free of the embossing pattern 40, as illustrated in FIGS. 6 and 8. The striped area 12 in FIGS. 6 and 8 does not illustrate the embossing pattern; instead the stripes only denote the embossed area. By discontinuous is meant that the embossing pattern comprises dots of different shapes which are not in contact with each other. The embossing pattern may form shapes giving a visual impression of a dotted line, flower, heart etc. The dots may have any shape and including conventional shapes such as circular, square, e.g. parallelogram, triangular. The size of an individual dot may vary from e.g. 0.01 mm² to 4 mm². The distance between the individual dots, i.e. the distance to the closest neighboring dot in any direction, may be for example from 0.2 to 5 mm. By providing embossing pattern the first region in the core may be visualized while higher stiffness and density in the area may be further promoted. Especially promoted stiffness and average density can be obtained when compression and embossing are performed in a same step.

In use, the transition 5, or transition area 5, of the absorbent article 1 is positioned between the two mentioned muscle tendons. Then transverse compression of the longitudinal edges 26 between the thighs of the user due to the lower average density of the edge region 26 comprising the acquisition sheet promotes formation of the correct 3-dimensional form of the article 1. In the embodiment shown in FIG. 8, the edge regions 26 also comprise core material, since the core has essentially the same extension as the liquid acquisition material. According to a further embodiment, the article does not comprise liquid acquisition material, but instead a large core 6, which extends over the transverse and longitudinal extension of the first region 12, and therefore, the edge regions 6 comprise core covered with a topsheet 30 and backsheet 31. In particular, the transverse compression of the longitudinal edges 26 of the core 6 between the tendons allows the front portion 2 and the second region 24 of the article 1 to fold upwards towards the user whereby the wetting zone raises and thus comes closer to the body and an upside side formed "bowl" shape can be formed in the central crotch portion, see FIG. 9. This allows closer, more secure fit of the article 1. Predetermined shaping of the article 1 also reduces the risk of the article folding in an undesired manner, for example creating channels which may cause leakage.

The centre region 25 is suitably thicker and softer than the first region 12. The centre region 25 provides a pre-formed raised portion, i.e. a preformed raised portion is provided. This is illustrated in FIG. 7. In addition, due to the fact that the average density of the absorbent core 6 is lower in the second region 24 than in the first region 12 and the fact that the facing sides 19, 20 of the respective leg portions 15, 16 converge backwards in the longitudinal direction of the article 1, the absorbent article 1 folds in use along the longitudinal centre line A effectively in at least parts of the crotch portion 3 and the rear portion 4. Thereby, the preformed raised portion in the centre region 25 is further enhanced during use in at least parts of the crotch portion 3. The raised portion is intended to make contact with the genitals of the wearer during use of the article 1. There may also be a raised portion provided in the rear section 38, which has a corresponding thickness as the centre region 25. Alternatively, the rear section 38 may be thinner than the centre region 25. This can be obtained for example by providing less absorbent material in the rear section 38 than in the centre region. Discharged bodily fluid can in this way be caught as soon as it leaves the body of the wearer and be absorbed immediately into the article instead of running out over the surface of the latter. The rear section 38 and the optional raised portion are accommodated in the cleft between the user's buttocks. This reduces the leakage from the rear of the article. More specifically, it provides very good protection against leakage via the cleft between the buttocks, which type of leakage usually occurs during the use of conventional absorbent articles when the user is sitting or lying on her back.

In case the article comprises a liquid acquisition sheet 36, the liquid acquisition sheet 36 may comprise a slit 39 as illustrated in FIG. 3 extending along the centre line A over at least part of the longitudinal extension of the second region 24. It should be noted that the slit 39 can be present in all embodiments of the article according to the present disclosure including at least one compression line although it has been shown only in FIG. 3. By the slit is meant a narrow longitudinally extending cut through, the acquisition layer material. The slit has a width in the transverse direction x that corresponds to an edge of a cutting knife and can be for example from 0.05 mm to 1 mm, but the width may be up to about 2 mm. By means of the slit, the second region 24 will be able to bend easily and thus conform to the body shape more effectively. In this way, the second region will be able to rise towards the body of the user when the legs of the user press the side edges of the article. Thus, the slit aids in positioning the product during the use, whereby the secure feeling, leakage control and comfort of the product may be further improved compared to the prior art products on the market.

The slit 39 can extend from a start point $a_{start}$ located in the centre line A in the rear portion 4 between the first region rear edge 37 and the core rear edge 57. The slit can extend up to the leg start point $a_0$ in the crotch portion 3. Preferably, the slit does not extend to the front portion 2 of the article, since the front portion preferably bends principally along a transverse bending axis. In this way the front portion will have maximal extension in the transverse direction and will thus be able to cover the pubic region of the user.

By providing the slit 39 so that it extends at least partially along the length of the rear section 38, a certain fold in the rear section is essentially promoted and the comfort of the hygiene article is improved. Therefore also undesired twisting, bunching or folding of the article between the buttocks is reduced. Folding of the rear section 38 in a controlled way by means of the slit 39 between the user's buttocks also promotes secure fit, as transverse and longitudinal movement of the article during wear is reduced. The different densities in the first region and at least a portion of the second region and the slit 39 in the acquisition layer cooperate in order to provide the article with a form that follows the contours of the wearer's body even more closely. More specifically, the article is provided with a form that molds towards labia during use. The side areas, i.e. edge regions, 26 comprising the acquisition layer can provide soft edges to the article which increases comfort.

Furthermore, since the width M of the first region 12 in the transition 5 essentially corresponds to the distance between the two mentioned muscle tendons on the wearer and in that the two side edges 22, 23 of the head part 13 of the first region 12 diverge forwards in the longitudinal direction from the transition 5, the absorbent article 1 can during use be anchored firmly with the transition 5 between the muscle tendons and be retained in this position. The front portion 2 of the article 1 is therefore held in the area in front of the mentioned muscle tendons, while the crotch portion 3 of the article 1 is effectively positioned correctly against the genitals of the wearer thanks to the slit 39 in the second region 24 enabling the core material underneath the liquid acquisition sheet in the centre region 25 to bulge upwards towards the body of the user when the legs of the user press the article from the sides, whereby a better fit and thus comfort can be obtained on the side of the article facing the body of the user. This helps to avoid problems associated with incorrect placement of the absorbent article 1, or movement of the article 1 during wear. In this way, the article 1 is prevented from moving backwards between the legs of the wearer. Even though a sanitary towel is fastened to the underwear in use, this is a common problem in conventional sanitary towels because the leg movements of the wearer often shift the sanitary towel backwards.

In addition, the higher average density of the first region 12 implies that it has great liquid-spreading capacity for rapid spreading of bodily fluid received from the wearer over the core 6. The higher average density of the first region 12 in the head part 13 also promotes stability, i.e. it promotes that the head part 13 remains out-stretched and that wrinkle formation is inhibited.

A suitable technique for manufacturing the absorbent cores of the present disclosure is mat-forming through an air-laying process. In the process an air-permeable mould is provided. Fibrous material is air-laid into the mould and the mould is filled, whereby an absorbent core is produced in with a desired amount of fibrous material.

After the absorbent core 6 is produced, it is pattern-compressed so that an absorbent core having regions with different densities is produced. Compressing may take place using any known means. The average density of the fibrous material in the non-compressed absorbent core corresponds to the average density of the absorbent core in the regions of lower average density, i.e. the second region 24. The absorbent core outside these regions, i.e. in the first region 12, is then compressed while within these regions, the core remains uncompressed.

Thus, the first region of the core is compressed more than the second region. A step of embossing of an embossing pattern can be performed simultaneously or subsequently with the compression to areas providing the first region. The embossing pattern is suitably visible through the top sheet.

The compression and embossing can be performed through the topsheet or the backsheet side of the core.

In the efficient mat-forming processes of today, mat-forming wheels are used, as described in U.S. Pat. No. 4,765,780, SE 9401542-7 and EP-A2-1 253 231. The air-permeable moulds are evenly spaced about the periphery of the mat-forming wheels. Fibrous material (together with any other material which might be desired) is fed from mills by means of blowers and onto mat-forming wheels via mat-forming covers. More than one mat-forming cover may be present per forming wheel and the concentration of the various components could differ in the different covers.

In an alternative to forming in mat-forming wheels, the absorbent cores of the present invention may be produced by laying fibrous material (together with any other material which might be desired) onto a web having a profile which ultimately gives a density difference on different parts of the material web. The material can be prefabricated and rolled up into rolls.

Alternatively, the absorbent core 6 can be produced by providing an air-permeable mould having the desired shape. The depth of the mould can vary according to the amount of material which is required at each point. Fibrous material is air-laid into the mould, and the mould is filled. Due to the differences in the mould depth in various areas, the amount of fibrous material at some points will vary. After the absorbent core is produced, it is compressed in those regions corresponding to the first region 12 and the second region 24 so that a uniform thickness is obtained in those regions. Thus, after the compression the thickness of the centre region 25 and/or the rear section 38 are greater than the thickness of the first region 12.

In this way, areas of different densities can be built up within the absorbent core 6. If desired, masks or baffles may be introduced in the mat-forming process, so that fibre-laying in the unmasked areas is higher than in the masked areas. Alternatively, the moulds may have different hole density and/or hole size in different areas of the mould. The flow of fibrous material will therefore be different in different areas of the mould. This allows further control over the material average density.

In addition to the absorbent core 6, the absorbent article 1 usually comprises, as shown in FIG. 1, a topsheet 30 and a backsheet 31. The topsheet 30 lies in direct contact with the wearer's body, and should therefore be soft, comfortable and liquid-permeable. The topsheet 30 can comprise a nonwoven material, e.g. spunbond, meltblown, carded, hydroentangled, wetlaid etc. Suitable nonwoven materials can be composed of natural fibres, such as wood pulp or cotton fibres, manmade fibres, such as polyester, polyethylene, polypropylene, viscose etc. or from a mixture of natural and man-made fibres. The topsheet material may further be composed of tow fibres, which may be bonded to each other in a bonding pattern, as e.g. disclosed in EP-A-1 035 818. Further examples of topsheet materials are porous foams, apertured plastic films etc. The materials suited as topsheet materials should be soft and non-irritating to the skin and be readily penetrated by body fluid, e.g. urine or menstrual fluid. The topsheet 30 may further be different in different parts of the absorbent article 1.

The backsheet 31 lies in contact with the wearer's garments, and is liquid-impermeable. The backsheet 31 refers to the liquid impervious material forming the outer cover of the absorbent article 1. The backsheet can comprise a thin plastic film, e.g. a polyethylene or polypropylene film, a nonwoven material coated with a liquid impervious material, a hydrophobic nonwoven material, which resists liquid penetration, or a laminate of a plastic film and a nonwoven material. Other laminate materials which are suitable for use as the backsheet are laminates of a nonwoven material and high loft material. The backsheet material may be breathable so as to allow vapour to escape from the absorbent core, while still preventing liquids from passing there through. Examples of breathable backsheet materials are porous polymeric films, nonwoven laminates of spunbond and meltblown layers and laminates of porous polymeric films and nonwoven materials. Preferably, the backsheet 31 comprises nonwoven material in at least the garment-facing surface thereof.

In the production method, the liquid-permeable topsheet material layer, a liquid-impermeable backsheet material layer and an absorbent material layer are fed to the manufacturing equipment. The core is arranged to be positioned in between the topsheet material layer and the backsheet material layer. The acquisition material layer is arranged to be positioned between the topsheet material layer and the absorbent material layer. The slit 39 is formed to the acquisition layer material by means of a knife at predetermined intervals. The core is formed as described above.

The topsheet 30 and the backsheet 31 and the acquisition sheet 36 each may extend with edge portions outside the absorbent core 6 around the core. The topsheet and the backsheet and optionally the acquisition sheet may be interconnected along edge portions to form a cover around the absorbent core 6. The acquisition sheet 36 may have a smaller extension than the topsheet and the backsheet. Suitably, at least the topsheet and the backsheet have substantially the same extension. The cover formed by the topsheet and the backsheet may extend outwards in the transverse direction to form flexible side flaps 32 or "wings", in the region of the crotch portion 3. The side flaps 32 are intended to be arranged around the crotch portion on the briefs of the wearer. Furthermore, the side flaps 32 are suitably provided with adhesive coating (not shown) on the backsheet 31, by means of which the wings 32 can be attached around the crotch portion on the briefs.

However, even if the absorbent article 1 shown in FIGS. 1 and 2 comprises wings 32, the absorbent article 1 may in variants of those embodiments not comprise any wings.

Furthermore, in an alternative embodiment, the absorbent article 1 may only comprise a backsheet 31, i.e. no topsheet. Additionally, the absorbent core 6 of the absorbent article may be wrapped in a single coversheet which can act as both inner and backsheet.

The absorbent article 1 defined above may comprise any attachment means known in the art to allow fastening to undergarments of a wearer. Such means may include a coating of adhesive or friction coating on the garment-facing surface of the article. Furthermore, the article 1 according to the invention may comprise, as above described, attachment flaps ("wings") which extend in the transverse direction of the article 1 and are intended to be arranged around the crotch portion on the briefs of the wearer. It is however important that the nature and placement of such attachment means does not significantly interfere with the function of the article 1 in use.

Although the above discussion has been exemplified through a sanitary napkin, the present invention is also applicable to other absorbent articles such as diapers, incontinence pads or panty-liners. For instance, application of the invention to diapers would provide similar benefits in terms of comfort, fit and leakage-prevention.

The invention should not be considered as limited by the above description; rather the scope and limitations of the invention are defined by the enclosed claims.

The invention claimed is:

1. A disposable hygiene article, wherein said article has a transverse direction (x), a longitudinal direction (y) and a longitudinal centre line (A) dividing the article into two mutually symmetrical and mirror-imaged portions (I) and (II), wherein said article has a front portion, a crotch portion and a rear portion, and said article comprises a liquid-permeable topsheet, a liquid-impermeable backsheet, an absorbent core arranged between the topsheet and backsheet, and optionally a liquid acquisition sheet arranged between the topsheet and the core, wherein an outer contour of the absorbent core is defined by mirror-imaged first and second core edge lines, and the core is delimited by a core front edge in the front portion and a core rear edge in the rear portion, wherein said absorbent core comprises a first region extending in the longitudinal direction (y) of the article from a first region front edge in the front portion over the crotch portion to the rear portion, and wherein the outer contour of the first region is defined by mirror-imaged first and second first region edge lines, and wherein said first region comprises a head part and two leg portions extending symmetrically about the centre line (A) and in a longitudinal direction (y) of the article, starting and diverging from a common leg portion start point ($a_0$) in the crotch portion and extending over a portion of the crotch portion towards separate leg portion endings in the rear portion, wherein a distance ($a_x$) between facing sides of the respective leg portions in the transverse direction (x) varies in the longitudinal direction (y), whereby a maximum distance ($a_1$) between the facing sides of the respective leg portions in the transverse direction (x) is in the crotch portion, located at a position in the longitudinal direction (y) corresponding to a position of a crotch point, wherein said facing sides of the respective leg portions converge backwards in the longitudinal direction (y) such that said distance ($a_x$) is reduced from said maximum distance ($a_1$) to a minimum distance ($a_2$), wherein said absorbent core further comprises a second region at least partially surrounded by said first region and extending between said leg portions in the transverse direction (x) and in the length direction (y) from the leg portion start point ($a_0$) in the crotch portion to an end point ($a_l$) in the rear portion wherein:

the first region has its narrowest width (M) in the transverse direction (x) in the front portion or at the location of a transition between the front portion and the crotch portion, the absorbent core in the crotch portion comprises a first rear compression line and a second rear compression line, wherein the lines mutually diverge in a direction towards the core front edge, and each of the lines has a diverging angle ($\alpha_2$; $\alpha_3$) of from 15-60° in respect of the extension of the centre line (A), wherein the lines have an extension up to the respective first and second first region edge lines and/or the respective first and second core edge lines; and wherein the second region has an average density which is at least 20% than the average density of the first region.

2. The disposable hygiene article according to claim 1, wherein the first and second rear compression lines are distanced from each other in the transverse direction (x) so as to be free from a common rear tip.

3. The disposable hygiene article according to claim 1, wherein the first and second rear compression lines form a V-shape comprising a common rear tip in which the lines meet, the tip having an imaginary contact point ($a_{80}$) with an imaginary rear division line dividing the article into the crotch portion and the rear portion.

4. The disposable hygiene article according to claim 1, wherein the absorbent core in the crotch portion comprises at least one compression line forming an essentially upside down turned V comprising a first leg and a second leg and a common front tip and, wherein the front tip is located on the centre line and has an imaginary contact point ($a_{50}$) with an imaginary front division line dividing the article into the front portion and the crotch portion, the first and second legs diverging towards the core rear edge at a mutual angle ($\alpha_1$) of from 30-120°, wherein the first and second legs extend up to the respective first and second first region edge lines or core edge lines.

5. The disposable hygiene article according to claim 4, wherein the front tip is distanced from a crotch point by 40-80 mm, and wherein the crotch point is located on the centre line (A) and is defined as a middle point of a centre region located centrally in the crotch portion.

6. The disposable hygiene article according to claim 1, wherein the compression lines are obtained by means of groove compressing the core and optionally the acquisition sheet and/or the topsheet with high pressure compression from the topsheet or the backsheet side of the article.

7. The disposable hygiene article according to claim 1, wherein the second region comprises a centre region extending symmetrically about the centre line (A) and having a longer extension in the longitudinal direction (y) than in the transverse direction (x), and a longitudinally and symmetrically about the centre line (A) extending rear section in contact with the centre region, and the centre region and the rear section being limited by the facing sides of the respective leg portions.

8. The disposable hygiene article according to claim 7, wherein the centre region comprises a weakening compression line extending along the centre line (A) between a start point ($a_0$) and a centre region end point ($a_e$).

9. The disposable hygiene article according to claim 7, wherein a maximum width ($a_1$) of the centre region is 10-50 mm and a length is from 50-110 mm, and the minimum width ($a_2$) of a rear section limited by the facing sides of the respective leg portions is 5-30 mm and a length is from 30-110 mm.

10. The disposable hygiene article according to claim 7, wherein the centre region extends in a thickness direction (D) of the article such that the centre region protrudes outwards from a plane of the first region.

11. The disposable hygiene article according to claim 1, wherein the first region has an average density of an absorbent material from 150-220 kg/m³, and the second region has an average density of an absorbent material from 70-150 kg/m³.

12. The disposable hygiene article according to claim 11, wherein the higher average density of the absorbent material is obtained by means of compression and/or providing an embossing pattern to the first region which covers at least portion of the first region, and wherein the second region is free of the embossing pattern.

13. The disposable hygiene article according to claim 12, wherein the first region is compressed more than the second region, and the first region is stiffer than the second region.

14. The disposable hygiene article of claim 12, wherein the embossing pattern comprises individual dots placed in a predetermined pattern.

15. The disposable hygiene article according to claim 1 further comprising the liquid acquisition sheet located between the topsheet and the core.

16. The disposable hygiene article according to claim 15, wherein the liquid acquisition sheet comprises airlaid nonwoven having a grammage of from 50-100 gsm.

17. The disposable hygiene article according to claim 15, wherein the liquid acquisition sheet comprises spunlace nonwoven having a grammage of from 30-90 gsm.

18. The disposable hygiene article according to claim 15, wherein the liquid acquisition sheet comprises high loft fibrous material having a grammage of from 30-90 gsm.

19. The disposable hygiene article according to claim 15, wherein the liquid acquisition sheet has a larger extension in both the transverse (x) and longitudinal (y) extension of the core and is located in contact with the core.

20. The disposable hygiene article according to claim 19, wherein the liquid acquisition sheet comprises high loft fibrous material, and wherein the first region of the core is embossed while the edge regions of the liquid acquisition sheet are free of an embossing pattern and/or compression.

21. The disposable hygiene article according to claim 1, wherein the narrowest width (M) of the first region of the core in said front portion is from 15 to 45 mm in the transverse direction (x).

22. The disposable hygiene article according to claim 1, wherein the second region covers from 10-50% of a total area of the core.

23. The disposable hygiene article according to claim 1, wherein the location of the smallest width (M) is distanced from the front tip in a longitudinal direction (y) by 0-10 mm.

24. A method for the manufacture of the disposable article according to claim 1, comprising the steps of:
  feeding a liquid-permeable topsheet material layer, a liquid-impermeable backsheet material layer and an absorbent material layer arranged to be positioned in between the topsheet material layer and the backsheet material layer, and optionally an acquisition material layer arranged to be positioned between the topsheet material layer and the absorbent material layer;
  forming the first region and second region of the core by compressing the first region more than the second region and/or by embossing an embossing pattern to areas providing the first region in the core; and
  providing at least the first rear compression line and the second rear compression line in the crotch region by means of high pressure compression from the topsheet or the backsheet side of the core.

25. The method according to claim 24, wherein the first region is formed prior to marriage of the backsheet to the absorbent core, topsheet and optionally liquid acquisition sheet of the article.

26. The disposable hygiene article according to claim 1, wherein the disposable hygiene article comprises one of a sanitary towel, a panty liner, an incontinence pad or a diaper.

27. The disposable hygiene article according to claim 1, wherein the second region has an average density which is at least 30% lower than the average density of the first region.

28. The disposable hygiene article according to claim 1, wherein the second region has an average density which is at least 50% lower than the average density of the first region.

29. The disposable hygiene article according to claim 11, wherein the first region has an average density of an absorbent material from 160-210 kg/m$^3$.

30. The disposable hygiene article according to claim 11, wherein the second region has an average density of an absorbent material from 80-130 kg/m$^3$.

31. The disposable hygiene article according to claim 29, wherein the second region has an average density of an absorbent material from 80-130 kg/m$^3$.

32. The method according to claim 24, further comprising providing a weakening compression line extending along the centre line (A) between the start point ($a_0$) and a centre region end point ($a_e$).

* * * * *

UNITED STATES PATENT AND TRADEMARK OFFICE
CERTIFICATE OF CORRECTION

| | |
|---|---|
| PATENT NO. | : 11,141,323 B2 |
| APPLICATION NO. | : 16/618969 |
| DATED | : October 12, 2021 |
| INVENTOR(S) | : Radne et al. |

It is certified that error appears in the above-identified patent and that said Letters Patent is hereby corrected as shown below:

In the Specification

In Column 2, Lines 16-17, change "Furthermore, it is an objective of the present disclosure to provide disposable hygiene article" to --Furthermore, it is an objective of the present disclosure to provide a disposable hygiene article--.

In Column 4, Lines 26-29, change "How the density is measured is described later in the detailed description, which is herein referred to. How the density is measured is described later in the detailed description, which is herein referred to." to --How the density is measured is described later in the detailed description, which is herein referred to.--.

In Column 4, Lines 45-46, change "which covers at least portion of the first region," to --which covers at least a portion of the first region,--.

In Column 4, Lines 51-52, change "In this way also aesthetically pleasant product can be provided." to --In this way, also an aesthetically pleasant product can be provided.--.

In Column 5, Line 35, change "and optionally and an acquisition" to --and optionally an acquisition--.

In Column 6, Lines 13-14, change "FIG. 6 schematically shows the first region and second region in disposable hygiene article" to --FIG. 6 schematically shows the first region and second region in a disposable hygiene article--.

In Column 6, Line 49, change "first longitudinal portion Ion a first side" to --first longitudinal portion I on a first side--.

In Column 10, Line 16, change "the leg start point ao an end point a1" to --the leg start point ao and end point a1--.

Signed and Sealed this
Eighteenth Day of October, 2022

*Katherine Kelly Vidal*

Katherine Kelly Vidal
*Director of the United States Patent and Trademark Office*

CERTIFICATE OF CORRECTION (continued)
U.S. Pat. No. 11,141,323 B2

In Column 10, Lines 34-39, change "The core may have different shapes, but the circumferential edges of the core define a shape in which a head portion and at least one neck area, i.e. an area with smaller width in the transverse direction, is located in the front portion or in the transition area of the core." to --The core may have different shapes, but the circumferential edges of the core define a shape in which a head portion and at least one neck area, i.e., an area with smaller width in the transverse direction, are located in the front portion or in the transition area of the core.--.

In Column 11, Lines 54-55, change "extend up to the respective the first and second first region" to --extend up to the respective first and second first region--.

In Column 12, Lines 32-34, change "Generally by stiffness is meant the extent of a material to resists deformation in response to an applied force." to --Generally by stiffness is meant the extent of a material to resist deformation in response to an applied force.--.

In Column 12, Lines 46-48, change "Therefore, for example the risk for deformation of the shape and thus for example movement 0.7 of the article during use is minimized." to --Therefore, for example the risk for deformation of the shape and thus for example movement of the article during use is minimized.--.

In Column 12, Lines 52-53, change "each extends and diverges towards the core front edge" to --each extend and diverge towards the core front edge--.

In Column 12, Lines 57-58, change "extend up to the respective the first and second first region" to --extend up to the respective first and second first region--.

In Column 15, Line 63, change "according to the present disclosure is shown." to --according to the present disclosure as shown.--.

In Column 16, Line 16, change "Thus, the two leg portion 15, 16 extend" to --Thus, the two leg portions 15, 16 extend--.

In Column 16, Lines 23-24, change "the absorbent article 1 vary along the longitudinal direction y" to --the absorbent article 1 varies along the longitudinal direction y--.

In Column 17, Lines 57-58, change "As explained above, the second region 24 is surrounded by the first region 12 is further constituted" to --As explained *above,* the second region 24 surrounded by the first region 12 is further constituted--.

In Column 19, Lines 18-19, change "FIGS. 6 and 8 schematically shows the regions in the article." to --FIGS. 6 and 8 schematically show the regions in the article.--.

In Column 19, Line 45, change "By providing embossing pattern the first" to --By providing an embossing pattern, the first--.

In Column 21, Lines 56-57, change "whereby an absorbent core is produced in with a desired amount of fibrous material." to --whereby an absorbent core is produced with a desired amount of fibrous material.--.

In Column 22, Lines 36-37, change "the rear section 38 are greater than the thickness of the first region 12." to --the rear section 38 is greater than the thickness of the first region 12.--.

In the Claims

In Claim 1, Column 24, Line 64, change "is at least 20% than the average density" to --is at least 20% lower than the average density--.

In Claim 12, Column 25, Lines 62-63, change "which covers at least portion of the first region," to --which covers at least a portion of the first region,--.